(12) United States Patent  
Iida et al.

(10) Patent No.: US 12,345,625 B2  
(45) Date of Patent: Jul. 1, 2025

(54) MICROSCOPIC OBJECT DETECTION DEVICE, DETECTION SYSTEM, AND DETECTION METHOD

(71) Applicants: University Public Corporation Osaka, Osaka (JP); Murata Manufacturing Co., Ltd., Nagaokakyo (JP)

(72) Inventors: Takuya Iida, Sakai (JP); Shiho Tokonami, Sakai (JP); Hiroki Ishikawa, Nagaokakyo (JP); Tsutomu Yamasaki, Nagaokakyo (JP); Hirohito Washida, Nagaokakyo (JP)

(73) Assignees: University Public Corporation Osaka, Osaka (JP); MURATA MANUFACTURING CO., LTD., Kyoto (JP)

( * ) Notice: Subject to any disclaimer, the term of this patent is extended or adjusted under 35 U.S.C. 154(b) by 219 days.

(21) Appl. No.: 17/921,420

(22) PCT Filed: May 7, 2021

(86) PCT No.: PCT/JP2021/017454  
§ 371 (c)(1),  
(2) Date: Oct. 26, 2022

(87) PCT Pub. No.: WO2021/225157  
PCT Pub. Date: Nov. 11, 2021

(65) Prior Publication Data  
US 2023/0194413 A1     Jun. 22, 2023

(30) Foreign Application Priority Data  
May 8, 2020   (JP) .................................. 2020-082483

(51) Int. Cl.  
*G01N 21/17* (2006.01)  
*G01N 21/64* (2006.01)  
*G01N 33/58* (2006.01)

(52) U.S. Cl.  
CPC ........ *G01N 21/171* (2013.01); *G01N 21/6456* (2013.01); *G01N 2021/1714* (2013.01); *G01N 33/582* (2013.01); *G01N 2201/06113* (2013.01)

(58) Field of Classification Search  
CPC ....... G01N 21/171; G01N 21/59; G01N 25/00; G01N 15/01; G01N 15/05; G01N 21/6486; G01N 2021/1714  
See application file for complete search history.

(56) References Cited

U.S. PATENT DOCUMENTS 6,934,087 B1 * 8/2005 Gutierrez ............. G02B 6/3833  
                                                      385/60  
10,495,573 B1 * 12/2019 Caubel ................... G01N 21/61  
(Continued)

FOREIGN PATENT DOCUMENTS

| CN | 1871058 A | 11/2006 |
|---|---|---|
| CN | 106660004 A | 5/2017 |

(Continued)

OTHER PUBLICATIONS

Official Communication issued in International Patent Application No. PCT/JP2021/017454, mailed on Jul. 20, 2021.

(Continued)

*Primary Examiner* — Uzma Alam  
*Assistant Examiner* — Justin J Van Cleave  
(74) *Attorney, Agent, or Firm* — Keating & Bennett, LLP

(57) ABSTRACT

A microscopic object detection system includes a collecting kit and a detection device. The collecting kit has a thin film for converting light into heat and is configured to be capable of holding a sample on the thin film. The detection device (Continued)

detects a plurality of microscopic objects in the sample by collecting the plurality of microscopic objects dispersed in the sample with the collecting kit. The detection device includes a laser module, an optical receiver, and a controller. The laser module emits a laser beam with which the collecting kit is irradiated. The optical receiver detects the laser beam from the sample held by the collecting kit and outputs a detection signal thereof. The controller calculates an amount of the plurality of microscopic objects collected in the sample based on a change of the detection signal over time.

12 Claims, 19 Drawing Sheets

(56) References Cited

U.S. PATENT DOCUMENTS

| | | | |
|---|---|---|---|
| 2006/0094109 A1* | 5/2006 | Trainer | G01N 35/0098 |
| | | | 435/808 |
| 2009/0027654 A1* | 1/2009 | Takahashi | G01N 21/78 |
| | | | 356/73 |
| 2011/0188039 A1* | 8/2011 | Aoyama | G01N 21/53 |
| | | | 356/338 |
| 2013/0252275 A1 | 9/2013 | Tokonami et al. | |
| 2015/0316480 A1 | 11/2015 | Seidel et al. | |
| 2016/0123968 A1 | 5/2016 | Iida et al. | |
| 2017/0074760 A1* | 3/2017 | Iida | C12M 1/26 |
| 2019/0242814 A1* | 8/2019 | Bachalo | G01N 21/85 |
| 2019/0357772 A1* | 11/2019 | Madsen | A61K 49/0097 |
| 2019/0383708 A1 | 12/2019 | Iida et al. | |
| 2020/0182770 A1 | 6/2020 | Tokonami et al. | |
| 2021/0033504 A1 | 2/2021 | Sun | |

FOREIGN PATENT DOCUMENTS

| | | | |
|---|---|---|---|
| CN | 108593416 A | 9/2018 | |
| CN | 108593910 A | 9/2018 | |
| CN | 108593916 A | 9/2018 | |
| CN | 109300569 A | 2/2019 | |
| CN | 109374894 A | 2/2019 | |
| CN | 109387633 A | 2/2019 | |
| JP | 2011-062607 A | 3/2011 | |
| JP | 2011062607 A1 * | 3/2011 | |
| JP | 2012-137485 A | 7/2012 | |
| KR | 20110100007 A | 9/2011 | |
| TW | 201738552 A1 * | 11/2017 | |
| WO | 2005023391 A2 | 3/2005 | |
| WO | 2012/077756 A1 | 6/2012 | |
| WO | 2014/192937 A1 | 12/2014 | |
| WO | 2015/170758 A1 | 11/2015 | |
| WO | 2017/195872 A1 | 11/2017 | |
| WO | 2017213107 A1 | 12/2017 | |
| WO | WO-2018159706 A1 * | 9/2018 | ............ B01J 19/00 |
| WO | 2018178213 A1 | 10/2018 | |
| WO | 2018207937 A1 | 11/2018 | |

OTHER PUBLICATIONS

Official Communication issued in corresponding Chinese Patent Application No. 202180032655.5, mailed on Jun. 3, 2024.
Wang et al., "In-Situ Measurement and Calculation of the Nanoparticle Transport Phenomena at the Counterflow Stagnation Plane", Journal of Engineering Thermophysics, vol. 38, No. 8, Aug. 2017, 5 pages.

* cited by examiner

<MULTI-POINT IRRADIATION MODE>

MICROSCOPIC OBJECT DETECTION DEVICE, DETECTION SYSTEM, AND DETECTION METHOD

TECHNICAL FIELD

The present disclosure relates to a microscopic object detection device, detection system, and detection method.

BACKGROUND ART

A technique for collecting a plurality of microscopic objects (microparticles, cells, microorganisms, etc.) dispersed in a liquid has been proposed. For example, WO 2017/195872 A (Patent Literature 1) and WO 2018/159706 A (Patent Literature 2) disclose techniques for collecting a plurality of microscopic objects dispersed in a liquid by light irradiation. When a photothermal conversion region that converts light into heat is irradiated with light, liquid in the vicinity of a light irradiation position is locally heated. As a result, microbubbles are generated and convection occurs in the liquid. Thus, a plurality of microscopic objects is carried toward the microbubbles by convection and collected around the light irradiation position.

CITATION LIST

Patent Literature

PTL 1: WO 2017/195872 A
PTL 2: WO 2018/159706 A

SUMMARY OF INVENTION

Technical Problem

It is desirable not only to collect a plurality of microscopic objects dispersed in a liquid by light irradiation but also to detect whether or not a plurality of microscopic objects is collected. In particular, it is desirable to quantitatively determine how much a plurality of microscopic objects is collected.

The present disclosure has been accomplished to address such a problem, and an object of the present disclosure is to collect a plurality of microscopic objects dispersed in a liquid and to obtain an amount of collected microscopic objects.

Solution to Problem (1) A detection device according to one aspect of the present disclosure detects a plurality of microscopic objects in a liquid sample by collecting the plurality of microscopic objects dispersed in the liquid sample with a collecting kit. The collecting kit has a photothermal conversion region that converts light into heat and is configured to hold the liquid sample on the photothermal conversion region. The microscopic object detection device includes a light source unit, an optical receiver, and a processor. The light source unit emits light with which the collecting kit is irradiated. The optical receiver detects light from the liquid sample held on the collecting kit and outputs a detection signal thereof. The processor calculates an amount of the plurality of microscopic objects collected in the liquid sample based on a change of the detection signal over time.

(2) The detection device heats the liquid sample by light irradiation of the photothermal conversion region to generate a bubble at a light irradiation position and generate convection in the liquid sample, and thereby collects the plurality of microscopic objects around the bubble.

(3) The processor calculates the amount of the plurality of microscopic objects collected in the liquid sample based on a slope of an approximate straight line obtained by regression of the detection signal in a predetermined period after start of light irradiation of the photothermal conversion region.

(4) The processor calculates the amount of the plurality of microscopic objects collected in the liquid sample based on an intensity ratio of two detection signals acquired along with light irradiation of the photothermal conversion region.

(5) The plurality of microscopic objects emits fluorescence when excited. The light source unit includes a laser light source that emits a laser beam with which the collecting kit is irradiated, and a fluorescent light source that emits light for exciting the plurality of microscopic objects.

(6) The laser light source and the fluorescent light source are integrated.

(7) The optical receiver includes a mask cutting light that does not need to be taken into the optical receiver in fluorescence emitted from the plurality of microscopic objects.

(8) The laser light source has a plurality of light emitting regions and emits a plurality of laser beams from the plurality of light emitting regions. The detection device further includes: a holder that holds the collecting kit; a condenser lens that collects the plurality of laser beams at a same focal point; an adjustment mechanism that adjusts a relative positional relationship between the holder and the condenser lens; and a controller that controls the adjustment mechanism. The controller is configured to switch between a single-point irradiation mode and a multi-point irradiation mode, each of which is a mode for irradiating the photothermal conversion region with at least a part of the plurality of laser beams. The single-point irradiation mode is a mode for controlling the adjustment mechanism so that the focal point coincides with the photothermal conversion region. The multi-point irradiation mode is a mode for controlling the adjustment mechanism so that the focal point is outside the photothermal conversion region.

(9) The laser light source includes a vertical cavity surface emitting laser.

(10) The condenser lens includes a graded-index optical fiber and a plano-convex lens. The optical fiber has a first end covering the plurality of light emitting regions and a second end bonded to a flat surface side of the plano-convex lens.

(11) The optical receiver is a single-pixel type photodetector.

(12) A detection system of microscopic objects according to one aspect of the present disclosure includes a collecting kit and a detection device. The collecting kit has a photothermal conversion region that converts light into heat and is configured to of hold a liquid sample on the photothermal conversion region. The detection device detects a plurality of microscopic objects in the liquid sample by collecting the plurality of microscopic objects dispersed in the liquid sample using the collecting kit. The detection device includes a light source unit, an optical receiver, and a processor. The light source unit emits light with which the collecting kit is irradiated. The optical receiver detects light from the liquid sample held on the collecting kit and outputs a detection signal thereof. The processor calculates an amount of the plurality of microscopic objects collected in the liquid sample based on a change of the detection signal over time.

(13) The collecting kit further includes: a first surface on which the photothermal conversion region is disposed; a second surface that holds the liquid sample between the first surface and the second surface; and a spacer for fixing a distance between the first surface and the second surface.

(14) A detection method according to still another aspect of the present disclosure is for detecting a plurality of microscopic objects in a liquid sample by collecting the plurality of microscopic objects dispersed in the liquid using a collecting kit. The collecting kit has a photothermal conversion region that converts light into heat and is configured such that liquid can be dropped on the photothermal conversion region. The detection method includes first to third steps. The first step is a step for irradiating the collecting kit with light. The second step is a step for detecting light from the liquid sample held on the collecting kit with an optical receiver. The third step is a step for calculating an amount of the plurality of microscopic objects collected in the liquid sample based on a change over time of a detection signal from the optical receiver.

Advantageous Effects of Invention

According to the present disclosure, it is possible to collect a plurality of microscopic objects dispersed in a liquid and to obtain an amount of collected microscopic objects.

DESCRIPTION OF EMBODIMENTS

Figure 1:
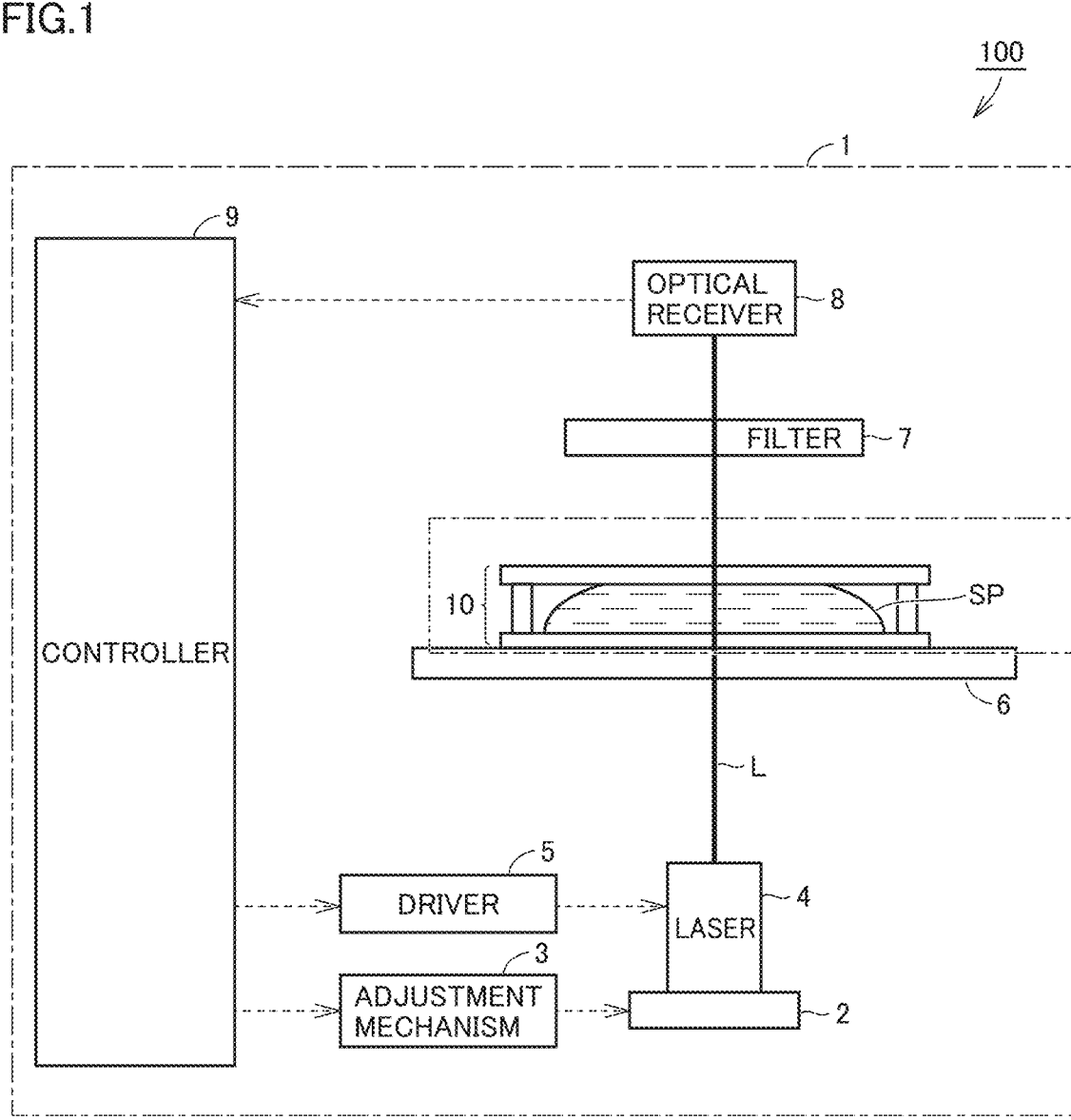
FIG. 1 is a block diagram schematically illustrating an overall configuration of a microscopic object detection system according to a first embodiment.

Embodiments of the present disclosure will now be described in detail with reference to the drawings. The same or corresponding parts in the drawings are denoted by the same reference signs, and the description thereof will not be repeated.

Definition of Terms

In the present disclosure, the wording "order of nanometers" includes a range from 1 nm to 1000 nm (=1 μm). The wording "order of micrometers" includes a range from 1 μm to 1000 μm (=1 mm). Therefore, the wording "order ranging from nanometers to micrometers" includes a range from 1 nm to 1000 μm. The wording "order ranging from nanometers to micrometers" typically indicates a range from several nm to several hundred μm, preferably indicates a range from 100 nm to 100 μm, and more preferably indicates a range from 1 μm to several tens of μm.

In the present disclosure, the term "microscopic object" means an object having a size on the order ranging from nanometers to micrometers. The shape of the microscopic object is not particularly limited, and examples of the shape include a spherical shape, an ellipsoidal shape, and a rod shape (rod shape). When the microscopic object has an ellipsoidal shape, at least one of the length in the major axis direction and the length in the minor axis direction of the ellipsoid may be on the order ranging from nanometers to micrometers. When the microscopic object has a rod shape, at least one of the width and the length of the rod may be on the order ranging from nanometers to micrometers.

Examples of the microscopic object include a metallic nanoparticle, a metallic nanoparticle aggregate, a metallic nanoparticle assembly structure, a semiconductor nanoparticle, an organic nanoparticle, a resin bead, and a particulate matter (PM). The "metallic nanoparticle" refers to a metallic particle having a size on the order of nanometers. The "metallic nanoparticle aggregate" refers to an aggregate formed by aggregation of a plurality of metallic nanoparticles. The "metallic nanoparticle assembly structure" refers to, for example, a structure in which a plurality of metallic nanoparticles is fixed to the surface of a base material (resin bead or the like) via interaction sites, and are arranged at intervals equal to or less than the diameter of the metallic nanoparticles with gaps therebetween. The "semiconductor nanoparticle" refers to a semiconductor particle having a size on the order of nanometers. The "organic nanoparticle" refers to a particle made of an organic compound having a size on the order of nanometers. The "resin bead" refers to a particle made of a resin having a size on the order ranging from nanometers to micrometers. The "PM" refers to a particulate substance having a size on the order of micrometers. Examples of the PM include PM 2.5 and suspended particulate matter (SPM).

The microscopic object may be a substance derived from a living body (biological substance). More specifically, the microscopic object may include cells, microorganisms (such as bacteria or fungi), biopolymers (such as proteins, nucleic acids, lipids, or polysaccharides), antigens (such as allergens), and viruses.

In the present disclosure, the term "honeycomb shape" means a shape in which a plurality of regular hexagons is arranged in a hexagonal lattice shape (honeycomb shape) in a two-dimensional direction. Each of the plurality of regular hexagons is formed with a pore. A structure body having a structure in which a plurality of pores is arranged in a honeycomb shape is referred to as a "honeycomb structure". Each pore has an opening on the order ranging from nanometers to micrometers. The pores may be through holes or non-through holes. In addition, the shape of the pores is not particularly limited, and may include any shape such as a cylindrical shape, a prismatic shape, and a spherical shape excluding a true spherical shape (for example, a semi-spherical shape or a semi-ellipsoidal shape).

In the present disclosure, the term "microbubble" means a bubble on the order of micrometers.

In the present disclosure, the wording "transmitting light" or "having light transmittance" means a phenomenon or property in which the intensity of light passing through a substance without being absorbed by the substance is greater than zero. Transmission of light includes scattering of light (forward scattering). The wavelength region of light may be any of a ultraviolet region, a visible region, and a near-infrared region, a region extending over two of these three regions, and a region extending over all of the three regions. It is only sufficient that the lower limit of the light transmittance range is greater than zero, and is not particularly limited. Note that the upper limit of the light transmittance range is 100%.

In the following, an x direction and a y direction represent the horizontal direction. The x direction and the y direction are orthogonal to each other. A z direction represents a vertical direction. The direction of gravity is downward in the z direction. Note that an upward direction in the z direction may be abbreviated as an upward direction, and a downward direction in the z direction may be abbreviated as a downward direction.

First Embodiment

<Overall Configuration of Detection System>

FIG. 1 is a block diagram schematically illustrating an overall configuration of a microscopic object detection system according to a first embodiment. A detection system 100 includes a detection device 1 and a collecting kit 10. Detection device 1 detects a plurality of microscopic objects in a liquid by collecting the plurality of microscopic objects dispersed in the liquid using collecting kit 10. Although FIG. 1 illustrates only one collecting kit 10, a plurality of collecting kits 10 is prepared as necessary and sequentially attached to detection device 1.

Detection device 1 includes a light source stage 2, an adjustment mechanism 3, a laser module 4, a driver 5, a sample holder 6, a filter 7, an optical receiver 8, and a controller 9.

Light source stage 2 is mounted with laser module 4. Light source stage 2 is, for example, an XYZ-axis stage, and is configured to be move in the x direction, the y direction, and the z direction.

Adjustment mechanism 3 is configured to adjust the positions of light source stage 2 in the x direction, the y direction, and the z direction in accordance with a command from controller 9. In the example described below, the relative positional relationship between laser module 4 mounted on light source stage 2 and collecting kit 10 is adjusted by adjusting the height (position in the z direction) of light source stage 2. However, the configuration of adjustment mechanism 3 is not particularly limited as long as the relative positional relationship between laser module 4 and collecting kit 10 can be adjusted. Adjustment mechanism 3 may adjust the position of collecting kit 10 with respect to stationary laser module 4, or may adjust the positions of both collecting kit 10 and laser module 4.

Laser module 4 is, for example, a semiconductor laser module. In the present embodiment, the wavelength of a laser beam L emitted from laser module 4 is included in the near-infrared region, and is, for example, 850 nm. The configuration of laser module 4 will be described in detail with reference to FIGS. 2 to 4. Although not illustrated, laser module 4 may be provided with a cooling device (such as a Peltier element) for cooling laser module 4. Note that laser module 4 is an example of a "laser light source" according to the present disclosure.

Driver 5 supplies a current for driving laser module 4 in accordance with a command from controller 9.

Sample holder 6 holds collecting kit 10. Similar to light source stage 2, sample holder 6 may also be an XYZ-axis stage as described above. Collecting kit 10 contains a sample SP. The configuration of collecting kit 10 will be described with reference to FIGS. 5 to 7.

Filter 7 is, for example, a neutral density (ND) filter. Filter 7 reduces the intensity of laser beam L emitted from laser module 4 to sample SP and transmitted through sample SP. Filter 7 is provided, as appropriate, according to the output (laser output) of laser beam L. Filter 7 may not be provided depending on the laser output.

Optical receiver 8 detects laser beam L whose intensity has been reduced by filter 7, and outputs a detection signal thereof to controller 9. In the present embodiment, optical receiver 8 is a single pixel type photodetector (single channel detector). Specifically, optical receiver 8 is a photodiode such as a PIN photodiode or an Avalanche photodiode (APD). It is to be noted, however, that, for example, a photoelectric tube or a photomultiplier may be used instead of the photodiode.

In addition, it is not necessary that optical receiver 8 is of a single pixel type. Optical receiver 8 may be a multi-pixel type photodetector (multi-channel detector). Specifically, optical receiver 8 may be a charged-coupled device (CCD) image sensor, a complementary metal-oxide-semiconductor (CMOS) image sensor, or the like.

Controller 9 is, for example, a microcomputer. Controller 9 includes a processor such as a central processing unit (CPU), a memory such as a read only memory (ROM) and a random access memory (RAM), and an input/output port (these components are not illustrated). Controller 9 controls the components (adjustment mechanism 3 and driver 5) constituting detection system 100. In addition, controller 9 calculates an amount of the microscopic objects collected in sample SP based on the detection signal from optical receiver 8. This calculation method will be described later.

<Configuration of Laser Module>

Figure 2:
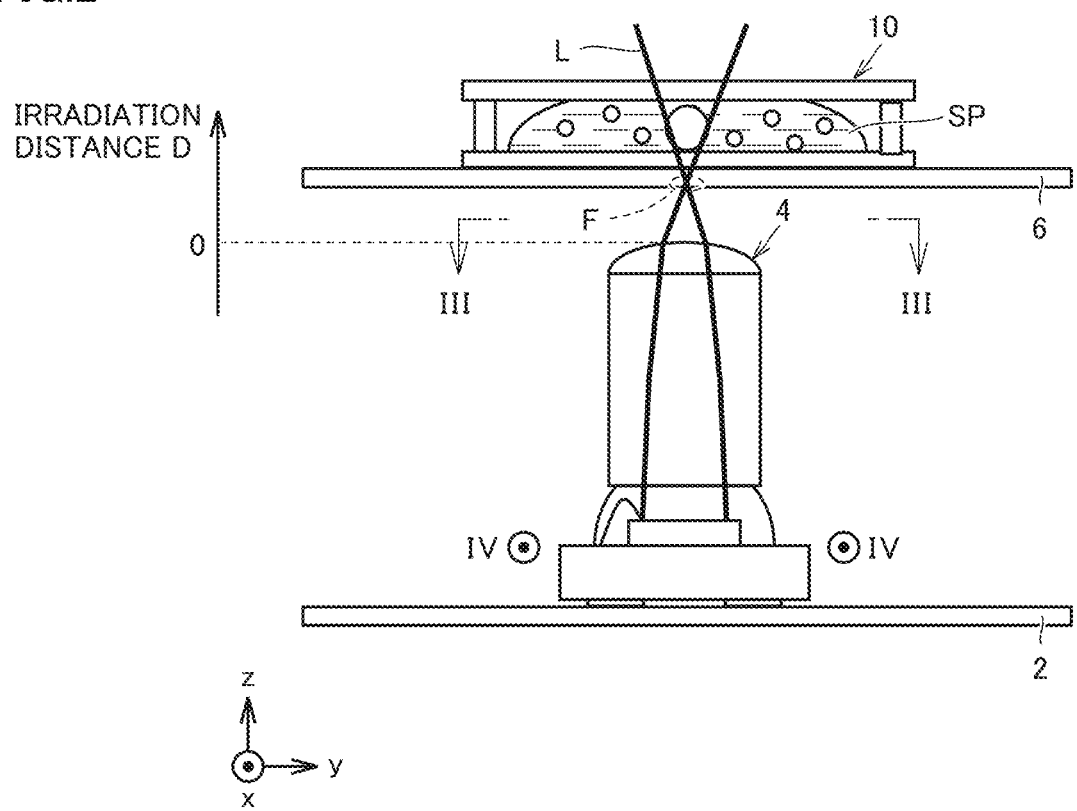
FIG. 2 is a diagram schematically illustrating a configuration of a laser module.

FIG. 2 is a diagram schematically illustrating a configuration of laser module 4. Laser module 4 is mounted on light source stage 2 and disposed below sample holder 6. Collecting kit 10 is mounted on sample holder 6. Collecting kit 10 on sample holder 6 is irradiated with laser beam L emitted upward from laser module 4.

Figure 3:
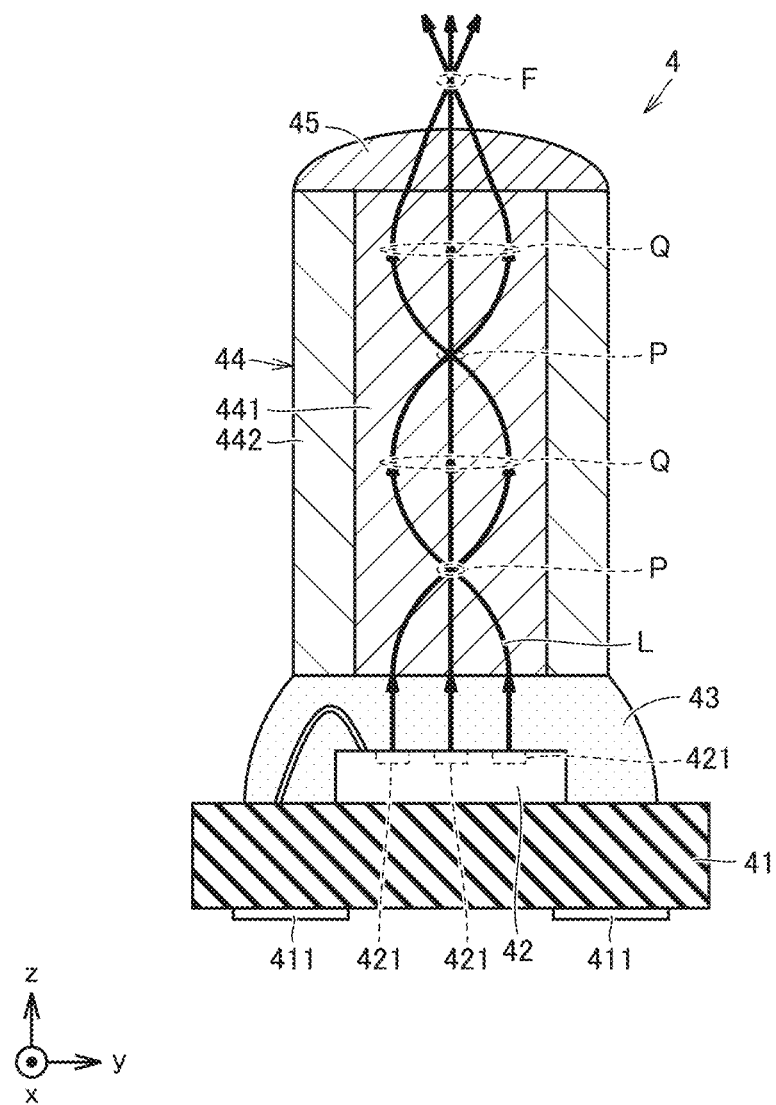
FIG. 3 is a cross-sectional view of the laser module taken along line in FIG. 2.
Figure 4:
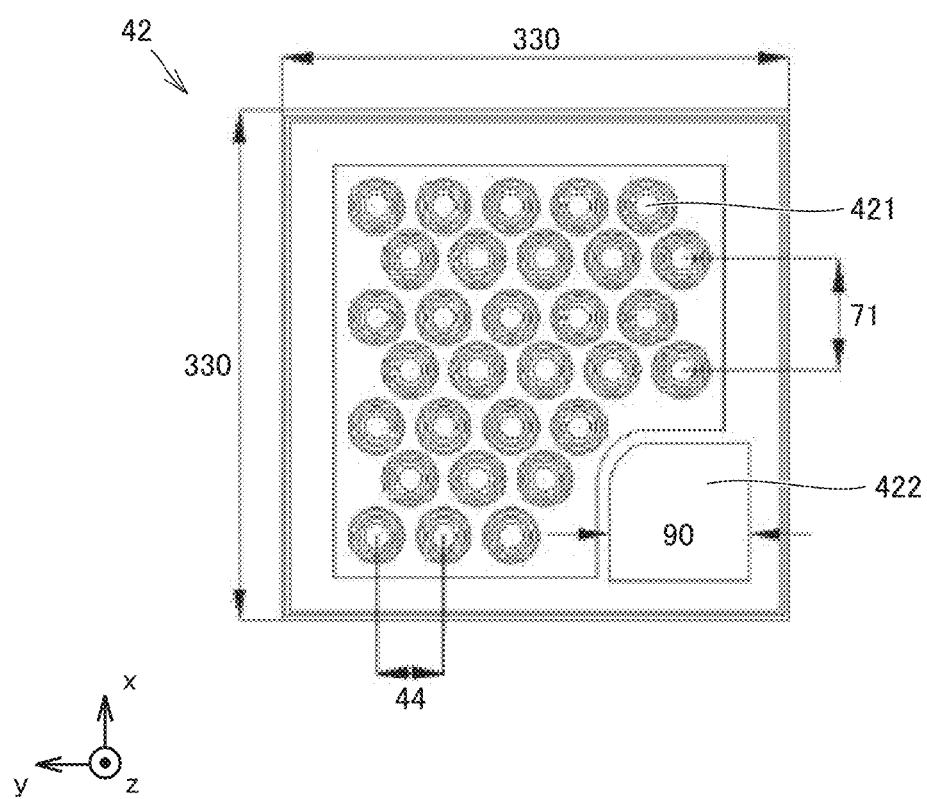
FIG. 4 is a cross-sectional view of the laser module taken along line IV-IV in FIG. 2.

FIG. 3 is a cross-sectional view of laser module 4 taken along line III-III in FIG. 2. FIG. 4 is a cross-sectional view of laser module 4 taken along line IV-IV in FIG. 2. Referring to FIGS. 3 and 4, laser module 4 includes a substrate 41, a surface emitting element 42, a bonding member 43, an optical waveguide 44, and a lens 45.

Substrate 41 is a flat plate made of an insulating material, and is, for example, a printed wiring board or a ceramic substrate. Surface emitting element 42 is mounted on the surface of substrate 41. A part of an electrode 411 is formed on the back surface of substrate 41. Electrode 411 is electrically connected to surface emitting element 42 by, for example, wire bonding. A drive current is supplied from driver 5 (see FIG. 1) to surface emitting element 42 via electrode 411.

Surface emitting element 42 is an array-type vertical cavity surface emitting laser (VCSEL). As illustrated in FIG. 4, surface emitting element 42 includes a plurality of (30 in this example) light emitting regions 421 and an electrode pad 422. The plurality of light emitting regions 421 is arranged in an array. All light emitting regions 421 emit light simultaneously, and each emits laser beam L. Emitted laser beams L are output in a direction (z direction) perpendicular to the surface of surface emitting element 42. The numerical values in FIG. 4 represent the dimensions (unit: μm) of each component.

Bonding member 43 is, for example, an adhesive, and bonds optical waveguide 44 onto surface emitting element 42. Bonding member 43 is made of a material transparent to light (in this example, near-infrared light) emitted from surface emitting element 42.

Optical waveguide 44 converges the plurality of laser beams L emitted from surface emitting element 42. The material of optical waveguide 44 is transparent to light emitted from surface emitting element 42, and is, for example, resin or glass. Optical waveguide 44 includes a core 441 and a cladding 442.

Core 441 has a cylindrical shape. An input end (corresponding to a "first end" according to the present disclosure) of core 441 is formed to cover all light emitting regions 421 so that all laser beams L emitted from surface emitting element 42 are incident thereon. Cladding 442 has a hollow cylindrical shape. Cladding 442 is formed so as to cover a side surface of core 441.

Lens 45 is a plano-convex lens and has a flat surface and a convex surface. The flat surface of lens 45 is joined to an output end (corresponding to a "second end" according to the present disclosure) of optical waveguide 44. The convex surface of lens 45 protrudes from a laser emission portion of laser module 4 in the light emission direction.

The propagation path of laser beam L in laser module 4 configured as described above will be described. Optical waveguide 44 is a graded index (GI) type optical fiber. Therefore, the refractive index of core 441 of optical waveguide 44 is the highest at the radial center of core 441, and smoothly decreases toward the outside in the radial direction. Laser beam L propagating inside core 441 has a plurality of modes having different propagation distances. Light of a low-order mode travels through the center of the core, and light of a high-order mode travels through a region outside the center of the core. The propagation distance of the light of the low-order mode is short, but the propagation speed of the light of the low-order mode is relatively low due to the high refractive index at the center of the core. On the contrary, in the light of the high-order mode, the propagation distance is long, but the propagation speed is relatively high. The refractive index distribution of core 441 is designed such that a difference in propagation time between the modes is sufficiently small.

The plurality of laser beams L propagating inside core 441 having such a refractive index distribution forms a node P and an antinode Q. Note that the positions of node P and antinode Q may change according to the wavelength of laser beam L. With respect to the traveling direction of laser beam L, the length of optical waveguide 44 is determined such that the output end of optical waveguide 44 is not positioned in the middle of the path from node P to antinode Q (in other words, the output end of optical waveguide 44 is located on the way from antinode Q to node P, or the output end of optical waveguide 44 coincides with antinode Q, as illustrated in FIG. 3). As a result, the plurality of laser beams L propagated through optical waveguide 44 is emitted from the output end of optical waveguide 44 in such a manner that they are converged. The plurality of emitted laser beams L is further converged by lens 45 to form the same focal point F.

<Configuration of Collecting Kit>

Figure 5:
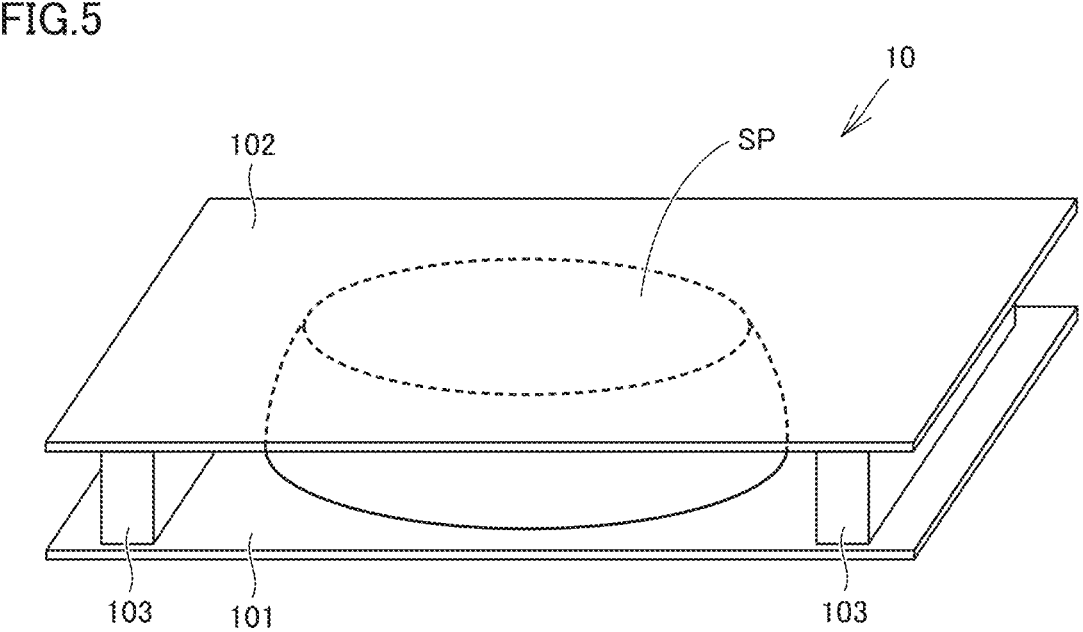
FIG. 5 is a perspective view of a collecting kit.

FIG. 5 is a perspective view of collecting kit 10. Collecting kit 10 includes a honeycomb substrate 101, a cover substrate 102, and a spacer 103.

Honeycomb substrate 101 is configured to generate heat by irradiation with laser beam L. In addition, honeycomb substrate 101 is formed of a material having light transparency. The configuration of honeycomb substrate 101 will be described with reference to FIGS. 6 and 7.

Sample SP is held (dropped) on the upper surface of honeycomb substrate 101. Sample SP is a liquid in which microscopic objects are dispersed. The type of the liquid (dispersion medium) is not particularly limited, and the liquid is ultrapure water in this example.

Cover substrate 102 is disposed above sample SP. That is, honeycomb substrate 101 and cover substrate 102 are provided so as to hold sample SP from above and below. Similar to honeycomb substrate 101, cover substrate 102 is formed of a light transmissive material (for example, glass or transparent resin). In the present embodiment, a cover glass is used as cover substrate 102. Note that (the upper surface of) the honeycomb substrate corresponds to a "first surface" according to the present disclosure. (The lower surface of) cover substrate 102 corresponds to a "second surface" according to the present disclosure.

Spacer 103 is provided on honeycomb substrate 101 and supports cover substrate 102. Spacer 103 is provided to fix the distance between honeycomb substrate 101 and cover substrate 102 to a prescribed value. Therefore, it is desirable to use a material (for example, a double-sided tape) having a controlled thickness for spacer 103. In a case where a plurality of collecting kits 10 is prepared, the distance (optical path length) laser beam L passes through sample SP has a common value by providing spacer 103. This makes it possible to reduce a variation in intensity of laser beam L transmitted through sample SP (in other words, to set measurement conditions of all collecting kits 10 to be the same).

Note that spacer 103 may be integrally formed with one of honeycomb substrate 101 and cover substrate 102. In addition, the shapes of honeycomb substrate 101 and cover substrate 102 are not limited to a sheet shape. Honeycomb substrate 101 and cover substrate 102 may be a part of a container having an internal space for holding sample SP.

Figure 6:
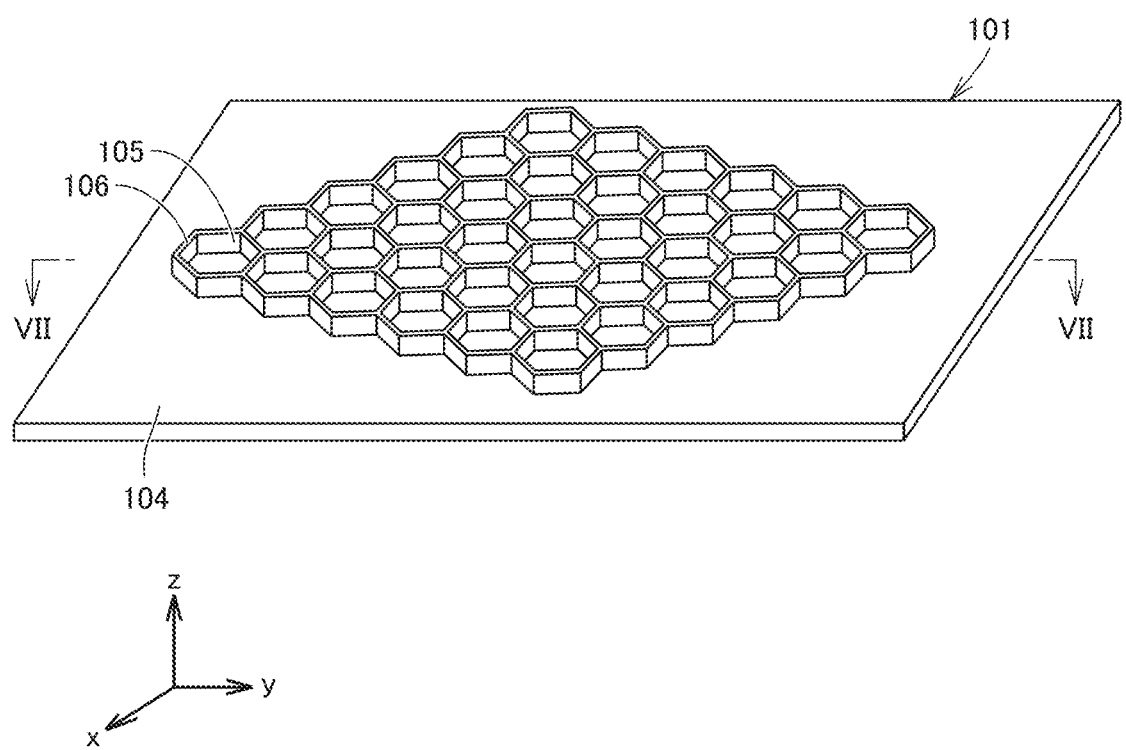
FIG. 6 is a diagram schematically illustrating a configuration of a honeycomb substrate.
Figure 7:
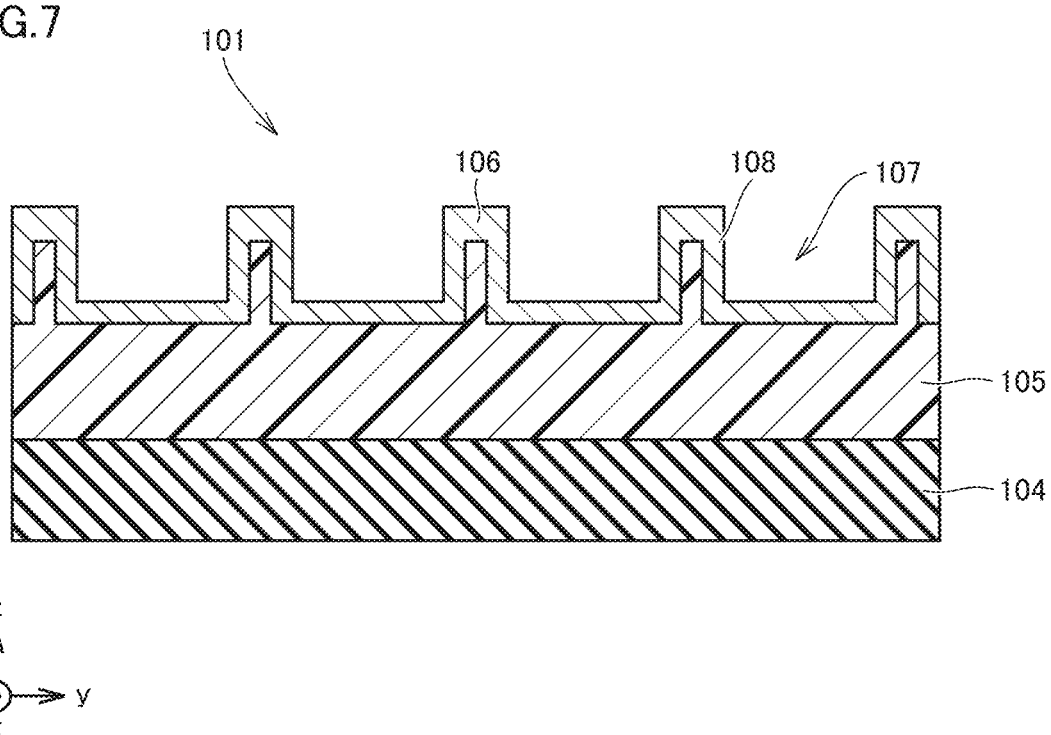
FIG. 7 is a cross-sectional view of the honeycomb substrate taken along line VII-VII in FIG. 6.

FIG. 6 is a diagram schematically illustrating the configuration of honeycomb substrate 101. FIG. 7 is a cross-sectional view of honeycomb substrate 101 taken along line VII-VII in FIG. 6. FIGS. 6 and 7 do not illustrate sample SP. Referring to FIG. 6, honeycomb substrate 101 includes a substrate 104, a honeycomb polymer film 105, and a thin film 106.

Substrate 104 is formed of a material that does not affect photothermal conversion (described later) of laser beam L by thin film 106. Examples of such a material include a transparent resin and glass. In the present embodiment, a transparent resin is used as substrate 104.

Honeycomb polymer film 105 is a polymer film in which a honeycomb structure is disposed on substrate 104. As a material of honeycomb polymer film 105, a polymer that can be dissolved in an organic solvent (hydrophobic solvent) is used. In the present embodiment, polystyrene is used as a matrix of honeycomb polymer film 105. A trace amount of an amphiphilic polymer having both a hydrophilic group and a hydrophobic group is added to the matrix.

Thin film 106 is formed on honeycomb polymer film 105. Thin film 106 absorbs laser beam L from laser module 4 and converts light energy into thermal energy. The material of thin film 106 preferably has high photothermal conversion efficiency in the wavelength region (near-infrared region in this example) of laser beam L. In the present embodiment, a gold thin film having a film thickness on the order of nanometers (specifically, 40 nm to 50 nm, for example) is formed as thin film 106. The gold thin film can be formed using a known method such as sputtering or electroless plating. Note that thin film 106 may not be formed on the entire surface of substrate 104, and may be formed on at least a part of substrate 104.

When thin film 106 is a gold thin film, free electrons on the surface of the gold thin film form surface plasmon and vibrate by laser beam L. This causes polarization. The energy of this polarization is converted into energy of lattice vibration by the Coulomb interaction between the free electron and the atomic nucleus. As a result, the gold thin film generates heat. In the following, this effect is referred to as a "photothermal effect".

The material of thin film 106 is not limited to gold, and may be a metal element other than gold (for example, silver) that can produce a photothermal effect, a metallic nanoparticle assembly structure (for example, a structure using gold nanoparticles or silver nanoparticles), or the like. Alternatively, the material of thin film 106 may be a material other than metal having a high light absorption rate in the wavelength range of laser beam L. Examples of such a material include a material close to a black body (for example, a carbon nanotube black body). The thickness of thin film 106 is determined by design or by experiment in consideration of the laser output and the absorption wavelength range and photothermal conversion efficiency of the material of thin film 106. The region where thin film 106 is formed corresponds to a "photothermal conversion region" according to the present disclosure.

Thin film 106 has a honeycomb structure reflecting the structure of honeycomb polymer film 105. Therefore, as illustrated in FIG. 7, thin film 106 includes a plurality of pores 107 in which a plurality of microscopic objects is captured and a plurality of partition walls 108 each separating adjacent pores among the plurality of pores 107 from each other (see Patent Literature 2 for the detailed configuration of honeycomb substrate 101). Thin film 106 is provided to cover at least a part of the plurality of pores 107 and the upper parts of the plurality of partition walls 108.

<Single-Point Irradiation Mode and Multi-Point Irradiation Mode>

Referring again to FIGS. 2 and 3, the distance from the tip of laser module 4 (the convex surface of lens 45) to the upper surface of collecting kit 10 along the emission direction (z direction) of laser beam L is referred to as an "irradiation distance D" below. As described with reference to FIG. 1, adjustment mechanism 3 is configured to be able to adjust the position of light source stage 2 in the z direction in accordance with a command from controller 9. Therefore, controller 9 can set irradiation distance D to any value by controlling adjustment mechanism 3.

Detection system 100 according to the first embodiment is configured to be switchable between a "single-point irradiation mode" and a "multi-point irradiation mode" by setting irradiation distance D. The single-point irradiation mode is a control mode for irradiating sample SP with single laser beam L. The multi-point irradiation mode is a control mode for irradiating sample SP with multiple (two or more) laser beams L.

Figure 8:
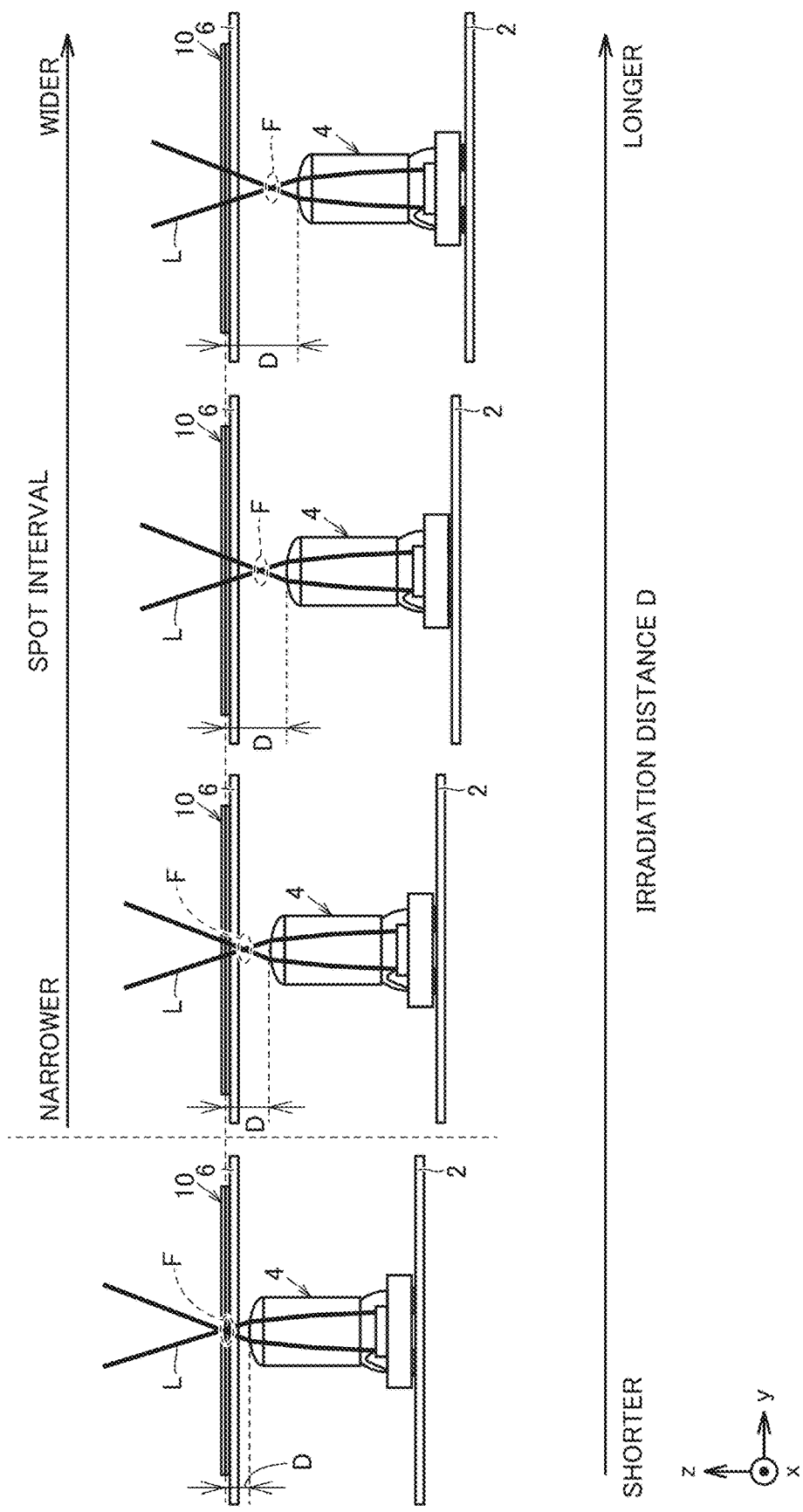
FIG. 8 is a diagram for describing a method for switching between a single-point irradiation mode and a multi-point irradiation mode.

FIG. 8 is a diagram for describing a method for switching between the single-point irradiation mode and the multi-point irradiation mode. Referring to FIGS. 2 and 8, the plurality of laser beams L emitted upward from the tip of laser module 4 is separate near lens 45, but intersects each other above lens 45 to form a focal point F. Then, the plurality of laser beams L is separated again above focal point F.

When controller 9 sets irradiation distance D so that the position of focal point F coincides with the upper surface of collecting kit 10, collecting kit 10 is irradiated with single laser beam L. That is, single-point irradiation of collecting kit 10 is achieved (single-point irradiation mode).

On the other hand, when controller 9 sets irradiation distance D such that the position of focal point F is lower than the upper surface of collecting kit 10, collecting kit 10 is irradiated with the plurality of laser beams L. That is, the multi-point irradiation of collecting kit 10 is achieved (multi-point irradiation mode). Although not illustrated in this example, controller 9 may set irradiation distance D such that the position of focal point F is above the upper surface of collecting kit 10 to achieve the multi-point irradiation.

In the multi-point irradiation mode, the interval between the plurality of laser beams L at the position of the upper surface of collecting kit 10 is referred to as a "spot interval". The spot interval becomes wider as the position of the upper surface of collecting kit 10 is located further upward from focal point F. Therefore, controller 9 can also set the spot interval to a desired value by adjusting irradiation distance D under the control of adjustment mechanism 3.

<Collecting Mechanism>

Figure 9:
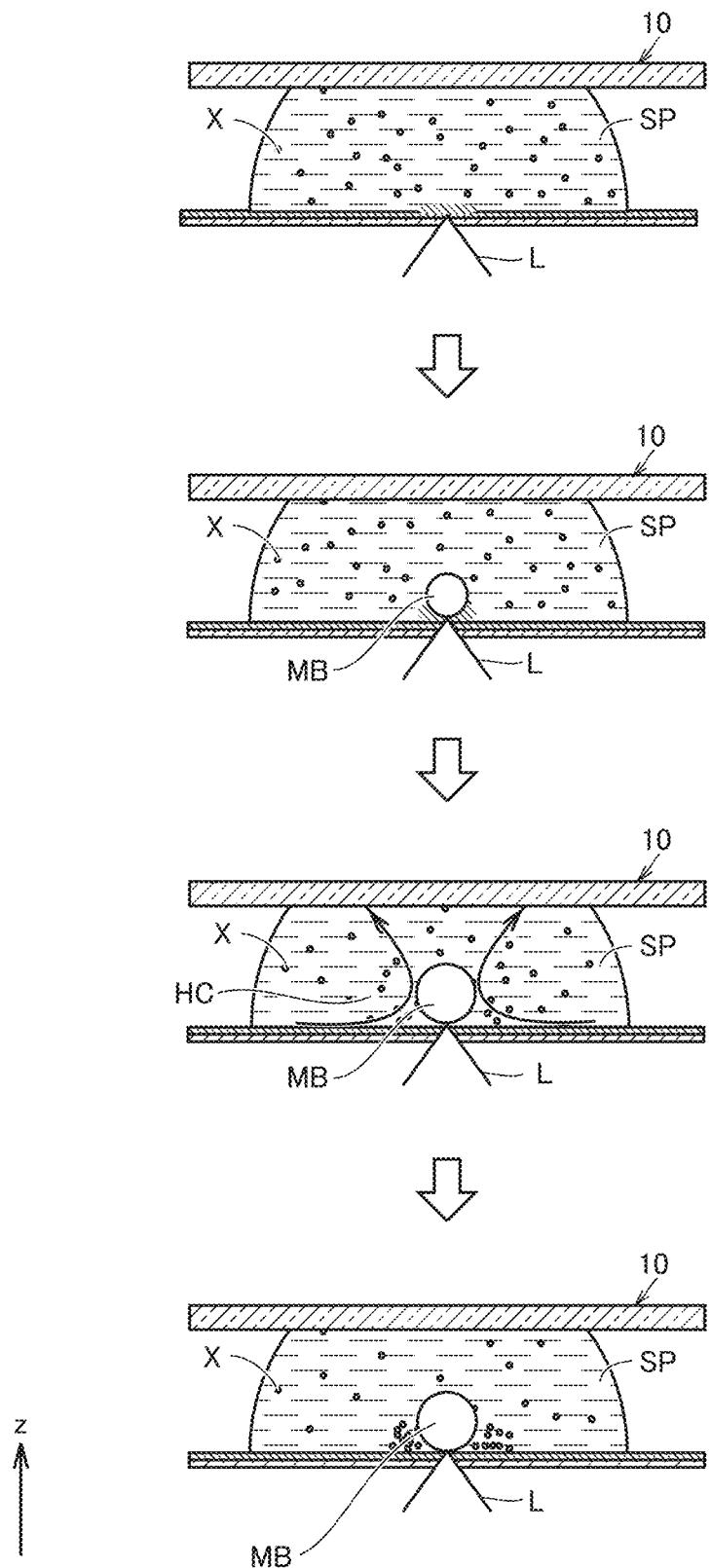
FIG. 9 is a diagram for describing a mechanism of collecting microscopic objects in the single-point irradiation mode.

FIG. 9 is a diagram for describing a mechanism of collecting microscopic objects in the single-point irradiation mode. When the irradiation with laser beam L is started, the vicinity of the laser spot is locally heated by the photothermal effect of thin film 106 at the laser spot. As a result, the dispersion medium of sample SP in the vicinity of the laser spot boils, and a microbubble MB is generated in the laser spot. The microbubble MB grows over time.

The closer to the laser spot, the higher the temperature of the dispersion medium. That is, a temperature gradient is generated in the dispersion medium by light irradiation. Due to this temperature gradient, regular heat convection (buoyancy convection) constantly occurs in the dispersion medium. The heat convection generated during single-point irradiation is once directed to microbubble MB and then moves away from microbubble MB as indicated by a reference sign HC.

The reason why heat convection occurs as described above can be described as follows. The dispersion medium present above the region where microbubble MB is generated becomes relatively thin by heating and rises by buoyancy. At the same time, a relatively low-temperature dispersion medium present in the horizontal direction of microbubble MB flows into microbubble MB.

Microscopic object X is carried toward microbubble MB on heat convection and collected in the vicinity of the laser spot. More specifically, a region (stagnation region) where the flow velocity of the convection is substantially zero is generated between microbubble MB and thin film 106, and microscopic object X carried by the heat convection is accumulated and collected in the stagnation region. Thereafter, when the irradiation with laser beam L is stopped, the heat convection is weakened and stops after a while.

Figure 10:
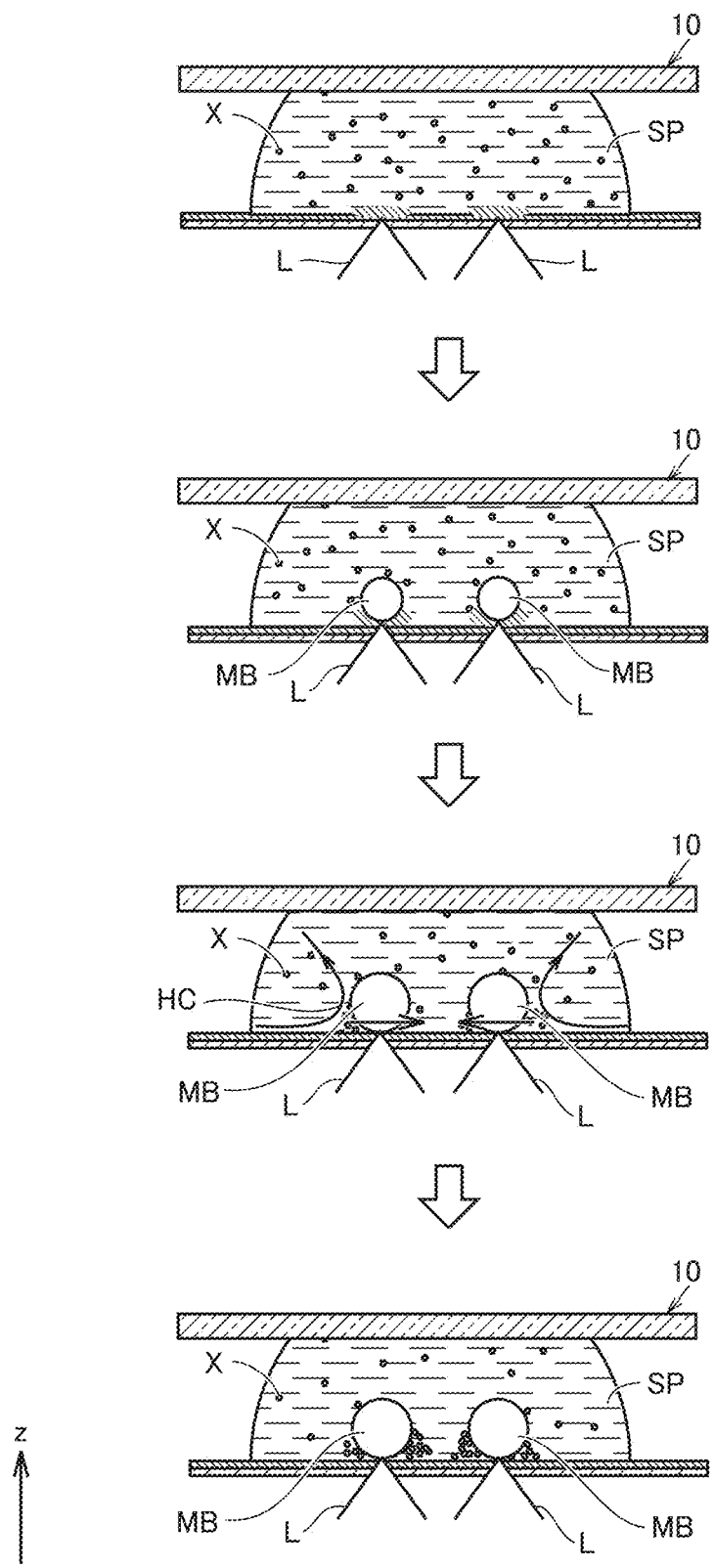
FIG. 10 is a diagram for describing a mechanism of collecting microscopic objects in the multi-point irradiation mode.

FIG. 10 is a diagram for describing a mechanism of collecting microscopic objects X in the multi-point irradiation mode. It is to be noted that FIG. 10 illustrates only two laser beams L in order to avoid complexity of illustration.

In the multi-point irradiation mode, microbubble MB is generated in the vicinity of each of multiple laser spots. Note that, depending on the spot interval, adjacent microbubbles MB may be integrated in the process of growth. Therefore, in the multi-point irradiation mode, microbubbles MB as many as the number of laser spots remain at the maximum. In the multi-point irradiation mode, microscopic object X is also carried by heat convection and accumulated and collected in the stagnation region of each microbubble MB, as in the single-point irradiation mode.

According to findings gained by the present inventors, rapid convection occurs toward the gap between adjacent microbubbles MB in the multi-point irradiation mode. Due to the influence of this convection, many microscopic objects X are collected in the stagnation region generated between adjacent microbubbles MB. As a result, when light irradiation conditions such as laser output are the same between the single-point irradiation mode and the multi-point irradiation mode, an amount of collected microscopic objects X can be greater in the multi-point irradiation mode.

<Collecting Flow>

Figure 11:
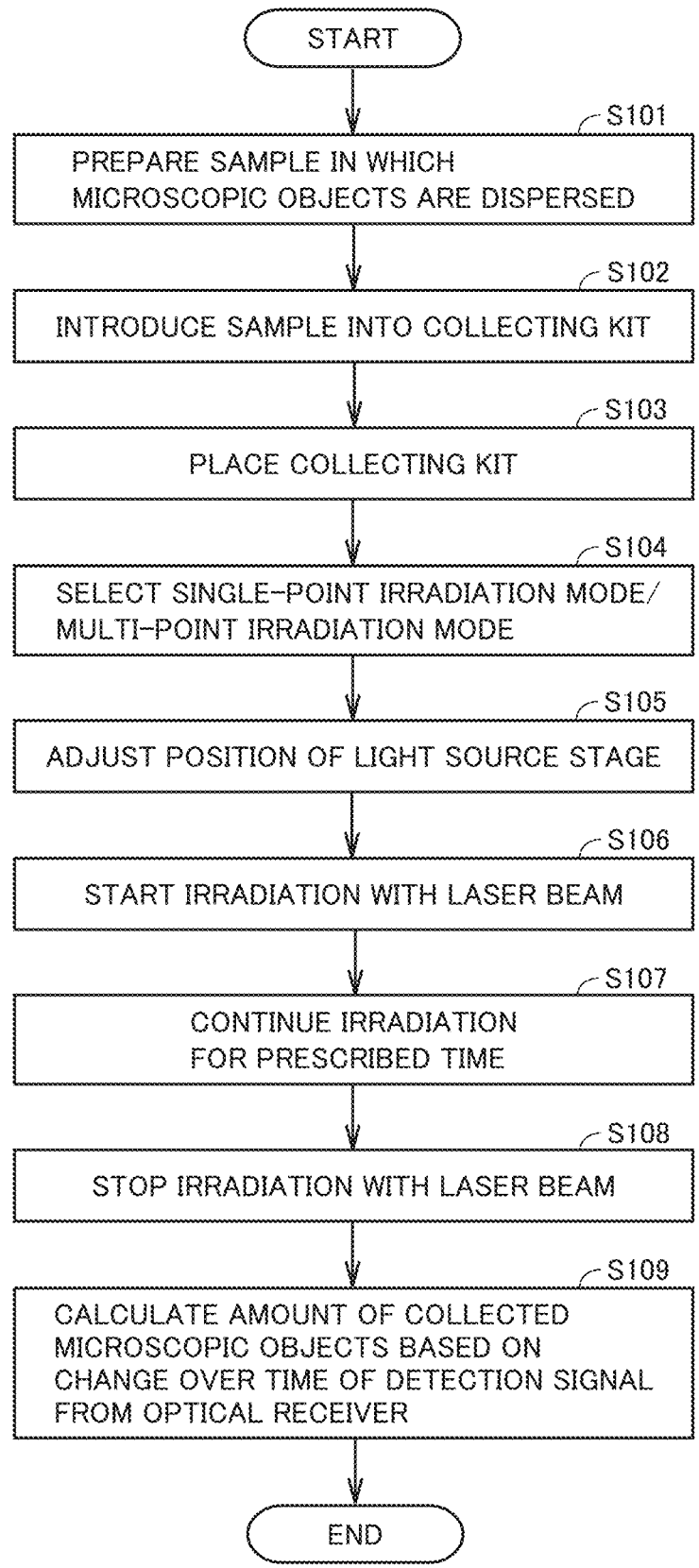
FIG. 11 is a flowchart illustrating a method for collecting microscopic objects in the first embodiment.

FIG. 11 is a flowchart illustrating a method for collecting microscopic objects in the first embodiment. Each step after step S104 in this flowchart is basically achieved by software processing by controller 9, but a part or all of the steps may be achieved by hardware (electric circuit) in controller 9. Controller 9 corresponds to both a "processor" and a "controller" according to the present disclosure. Note that the "processor" and the "controller" according to the present disclosure may be separate devices.

In step S101, sample SP which is a liquid in which microscopic objects are dispersed is prepared. Prepared sample SP is introduced into collecting kit 10 (step S102). More specifically, a predetermined amount of sample SP is dropped on honeycomb substrate 101. Then, cover substrate 102 is put above sample SP. Collecting kit 10 prepared for measurement in this manner is placed on sample holder 6 (step S103).

In step S104, controller 9 selects either one of the control modes, the single-point irradiation mode or the multi-point irradiation mode, based on a user operation. When the multi-point irradiation mode is selected, the spot interval can also be set by the user.

Appropriate position and height (irradiation distance D) of light source stage 2 are determined in advance for each control mode (single-point irradiation mode or multi-point irradiation mode). Controller 9 adjusts the position of light source stage 2 by controlling adjustment mechanism 3 according to the selected control mode (step S105). The position in the vertical direction of focal point F where all laser beams L are collected is known from the specification (wavelength of laser beam L, shapes of optical waveguide 44 and lens 45, and the like) of laser module 4. Therefore, controller 9 can set irradiation distance D to a desired value by appropriately adjusting the height of light source stage 2 from the initial height.

In step S106, controller 9 controls driver 5 to start irradiation with laser beam L. Controller 9 continues the irradiation of collecting kit 10 with laser beam L for a prescribed time (step S107). The prescribed time is typically about several 10 seconds to several minutes, and can be set by the user. Along with this light irradiation, microscopic objects are collected. After the light irradiation for the prescribed time, controller 9 controls driver 5 to stop the irradiation of collecting kit 10 with laser beam L (step S108).

During the execution of steps S106 to S108, controller 9 continuously or intermittently acquires the detection signal of laser beam L from optical receiver 8. In step S109, controller 9 calculates an amount of the microscopic objects (amount of collected microscopic objects) collected by irradiation with laser beam L based on a change over time of the detection signal. This calculation method will be described later. Thus, a series of processes ends.

<Calculation of Amount of Collected Microscopic Objects>

Next, a result of collecting the microscopic objects and calculating an amount of collected microscopic objects will be described based on an actual measurement result. Here, resin beads are employed as an example of the microscopic objects. The material of the resin beads is polystyrene. However, the material of the resin beads is not limited thereto, and may be acryl, polyolefin, polyethylene, polypropylene, or the like.

Figure 12:
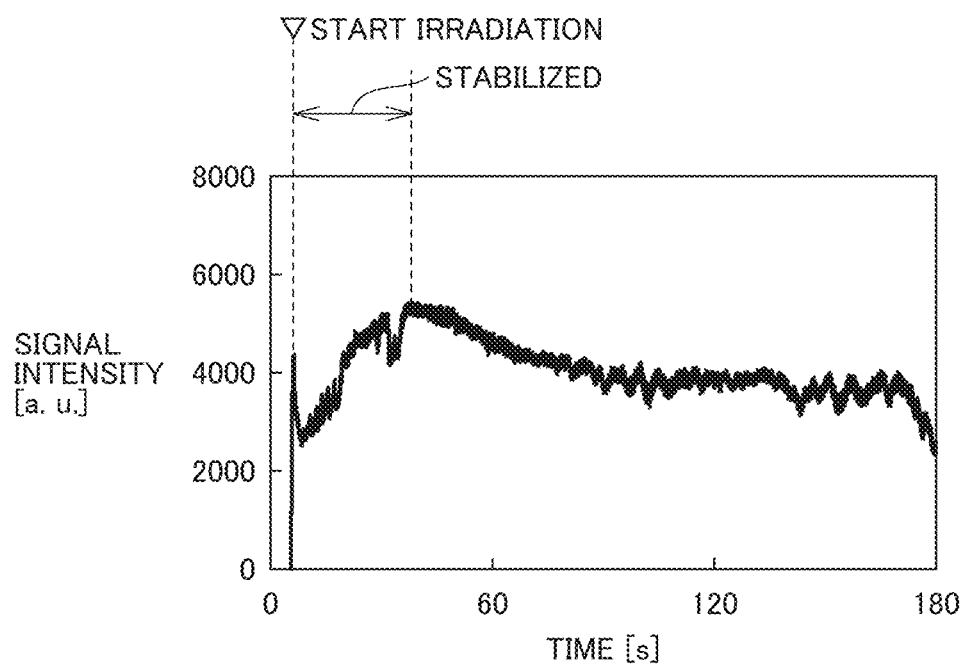
FIG. 12 is a diagram illustrating an example of a change over time of a detection signal from an optical receiver.
Figure 14:
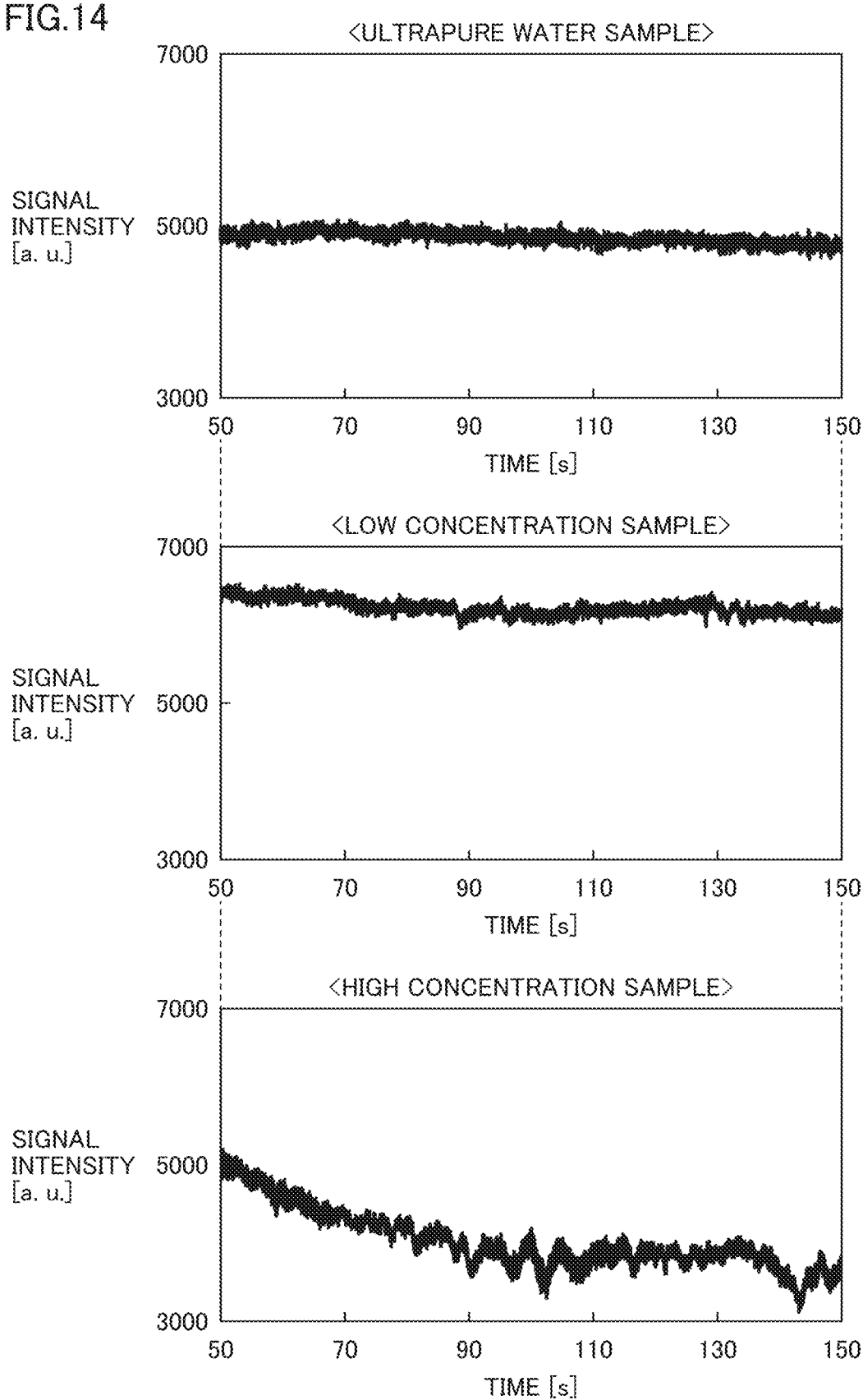
FIG. 14 is a diagram for comparing detection signals from an optical receiver 8 in a case where three types of samples are used.

FIG. 12 is a diagram illustrating an example of a change over time of the detection signal from optical receiver 8. In FIG. 12 and FIG. 14 described later, the horizontal axis represents elapsed time. The vertical axis represents the intensity of the detection signal from optical receiver 8.

In the measurement example shown in FIG. 12, the concentration of the resin beads in sample SP was $1.01 \times 10^8$ [particles/mL]. The diameter of the resin beads was 1.0 μm. The resin beads do not contain a fluorescent dye. The liquid volume of sample SP was 20 μL. The output (laser output) of laser beam L emitted to sample SP was 180 mW. The irradiation time of laser beam L was set to 180 seconds.

Referring to FIG. 12, it took about 30 seconds from the start of irradiation with laser beam L to stabilize the laser output. After the laser output is stabilized, the intensity of the detection signal gradually decreased over time. At the time of irradiation for 180 seconds, the intensity of the detection signal was substantially constant.

Figure 13:
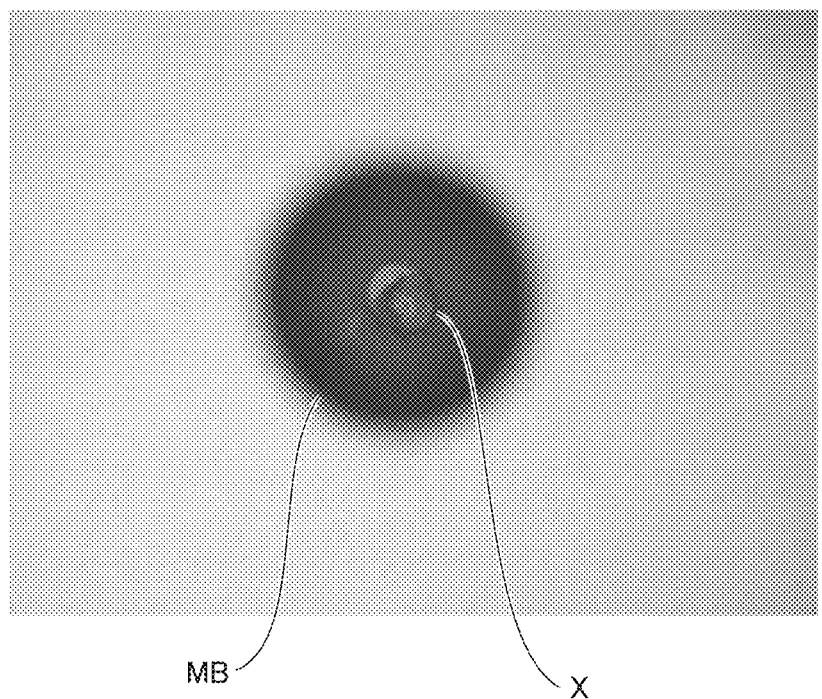
FIG. 13 is a transmission image of a sample when irradiation with a laser beam is stopped.

FIG. 13 is a transmission image of sample SP when irradiation with laser beam L is stopped. This image is acquired by imaging sample SP from below using an imaging device (image sensor) (not illustrated). As shown in FIG. 13, it is confirmed that microscopic objects X (resin beads) are collected around the portion irradiated with laser beam L (laser spot).

FIG. 14 is a diagram for comparing detection signals from optical receiver 8 in a case where three types of samples SP are used. In this example, three types of samples SP were prepared which were a sample using only ultrapure water containing no resin beads, a sample having resin beads with a concentration of $1.01 \times 10^8$ [particles/mL], and a sample having resin beads with a concentration of $1.01 \times 10^9$ [particles/mL]. These samples are referred to in order as "ultrapure water sample", "low concentration sample" and "high concentration sample". The liquid volume was 20 μL in any sample. The output (laser output) of laser beam L was 180 mW. The irradiation time of laser beam L was set to 180 seconds.

Referring to FIG. 14, in the ultrapure water sample, the intensity of the detection signal was almost constant. In the low concentration sample, the intensity of the detection signal decreased slightly over time. In the high concentration sample, the intensity of the detection signal more remarkably decreased over time as compared with the low concentration sample.

For a period from 50 seconds to 150 seconds using the irradiation start time of laser beam L as a reference point, a time function (a decrease rate of the detection signal) of the detection signal of each sample was linearly regressed by the method of least squares to calculate a slope of an approximate straight line. As a result, the slope of the approximate straight line in the ultrapure water sample was −1.68. The slope of the approximate straight line in the low concentration sample was −2.18. The slope of the approximate straight line in the high concentration sample was −11.04. These values are average values of measurement results performed three times for each sample.

As described above, by following the attenuation state of the detection signal acquired from optical receiver 8, the concentration of the resin beads contained in sample SP can be quantitatively calculated. Specifically, the correlation between the concentration of the resin beads and the slope of the approximate straight line is experimentally determined in advance. Then, the correlation is obtained as a table, a map, or the like and stored in the memory of controller 9. As a result, the slope of the approximate straight line can be calculated from the detection signal from optical receiver 8, and the concentration of the resin beads can be calculated from the slope of the approximate straight line.

Figure 15:
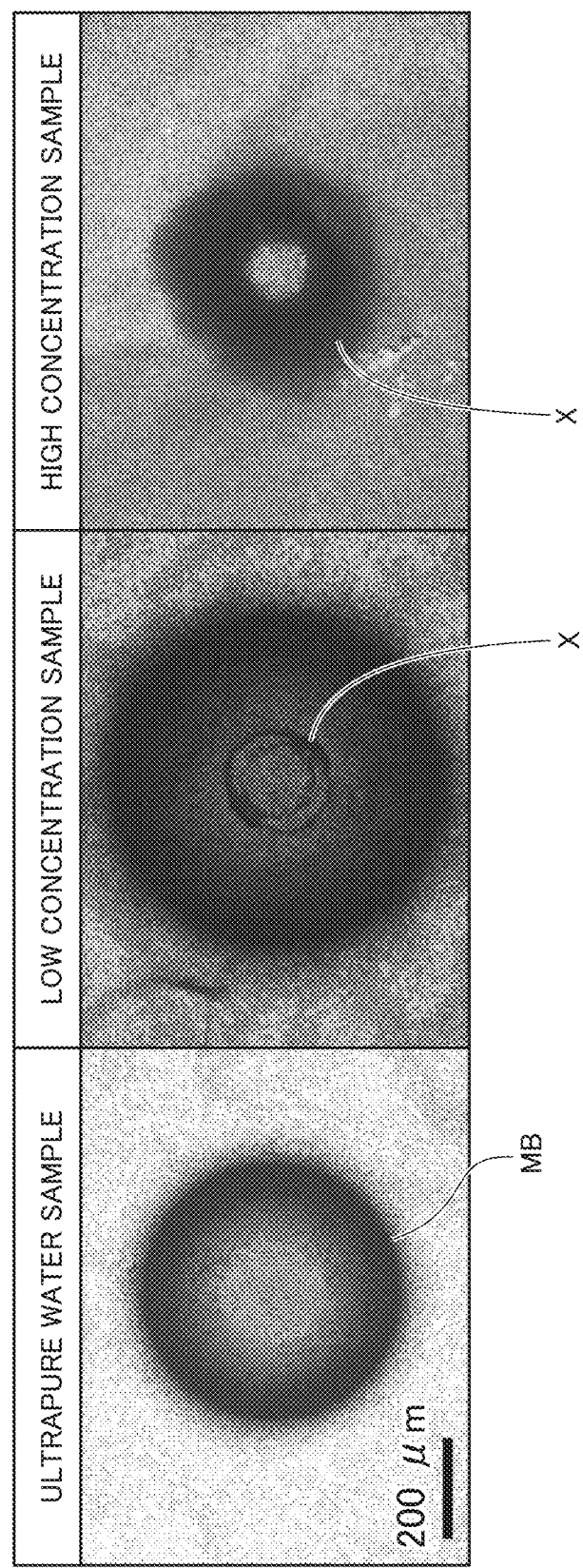
FIG. 15 is an image showing results of collecting resin beads in three types of samples.

FIG. 15 shows images indicating results of collecting resin beads in three types of samples SP. It can be confirmed from FIG. 15 that, in the low concentration sample, the resin beads (microscopic objects X) were collected in the stagnation region generated in the central portion of microbubble MB. It can be confirmed that, in the high concentration sample, many resin beads are collected not only in the stagnation region but also around microbubble MB. It is considered that the collection of the resin beads around microbubble MB causes great attenuation of the detection signal.

As described above, in the first embodiment, the microscopic objects are collected by irradiating sample SP having the microscopic objects dispersed therein with laser beam L. During the collecting process, a transition of the detection signal (transmission amount) of laser beam L transmitted through sample SP is acquired using optical receiver 8. In the first embodiment, the correlation between a decrease rate of the detection signal of laser beam L (slope of the approximate straight line) and an amount of the collected microscopic objects is obtained in advance. Therefore, according to the first embodiment, an amount of collected microscopic objects can be obtained by calculating the decrease rate of the detection signal of laser beam L while using laser beam L to collect the microscopic objects in the liquid.

The absolute value of the detection signal of laser beam L does not necessarily indicate the amount of collected microscopic objects. This will be understood from the measurement results, shown in FIG. 14, indicating that, for example, the intensity of laser beam L in the low concentration sample is greater than the intensity of laser beam L in the ultrapure water sample. It is considered that this is because various factors such as a difference in the size of microbubbles MB generated by light irradiation can affect the absolute value of the intensity of laser beam L. According to the first embodiment, the amount of collected microscopic objects can be quantitatively evaluated by using the decrease rate of the detection signal (that is, a change over time of the detection signal) instead of the absolute value of the detection signal.

Modification of First Embodiment

In the example described with reference to FIG. 15, the decrease rate of the detection signal of laser beam L is used, but a parameter that can be used for calculating the amount of collected microscopic objects is not limited thereto. An example of using an intensity ratio (more specifically, attenuation ratio) of the detection signals before and after irradiation with laser beam L will be described below.

Figure 16:
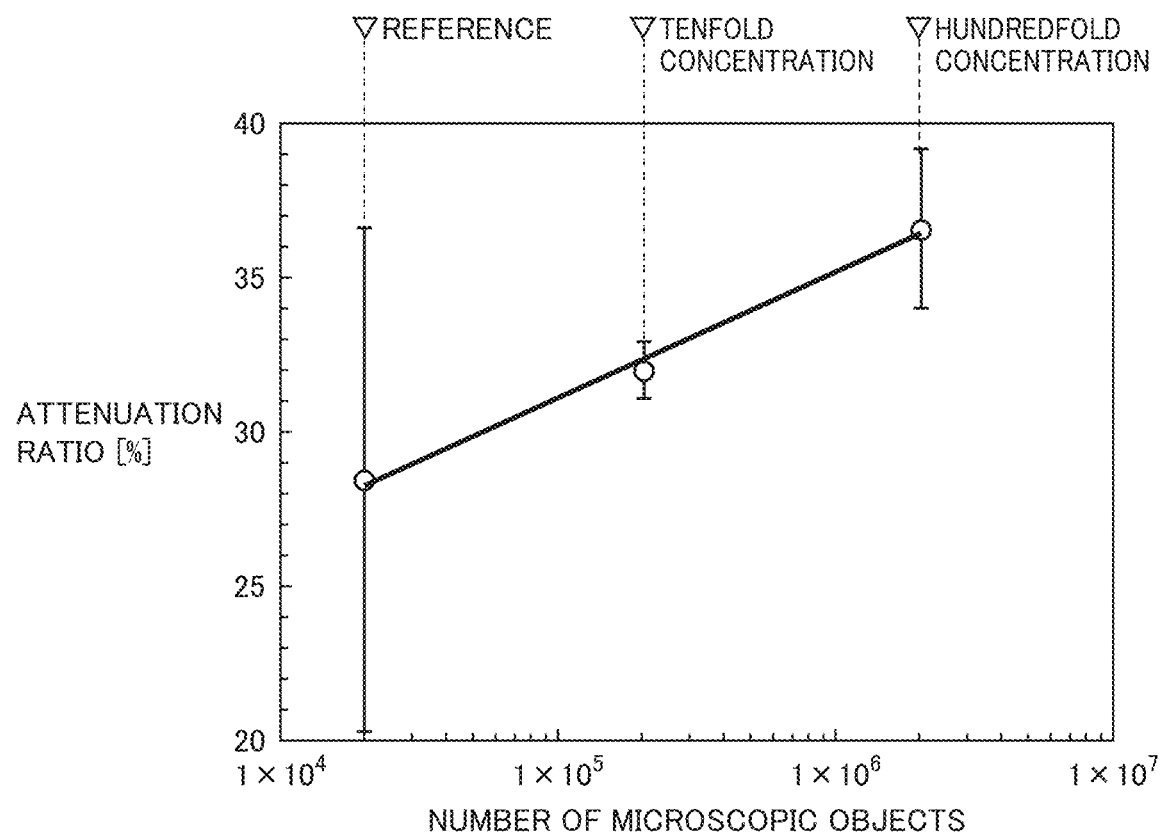
FIG. 16 is a diagram illustrating a relationship between the number of resin beads and an attenuation ratio of a detection signal.

FIG. 16 is a diagram illustrating a relationship between the number of resin beads and an attenuation ratio of the detection signal. In FIG. 16, the horizontal axis represents the number of resin beads on a logarithmic scale. The vertical axis represents the attenuation ratio of the detection signal from optical receiver 8.

The attenuation ratio of the detection signal can be calculated according to following Expression (1). In Expression (1), the intensity of the detection signal at the start of irradiation with laser beam L (0 seconds) is described as RX1, and the intensity of the detection signal at the end of irradiation with laser beam L (180 seconds) is described as RX2. As understood from Expression (1), the attenuation ratio of the detection signal is an example of an intensity ratio of two detection signals acquired after the start of irradiation with the laser beam (in a broader sense, an example of a change over time of the detection signal).

$$\text{Attenuation ratio} = 100 \times (1 - RX2/RX1) \qquad (1)$$

It can be seen from FIG. 16 that high linearity is exhibited when the correlation between the number of resin beads (which may be the concentration of resin beads) and the attenuation ratio of the detection signal is plotted on a semi-logarithmic graph. The correlation having such linearity is obtained in advance and stored in the memory of controller 9. As a result, the number of resin beads can be calculated from the attenuation ratio of the detection signal.

Figure 17:
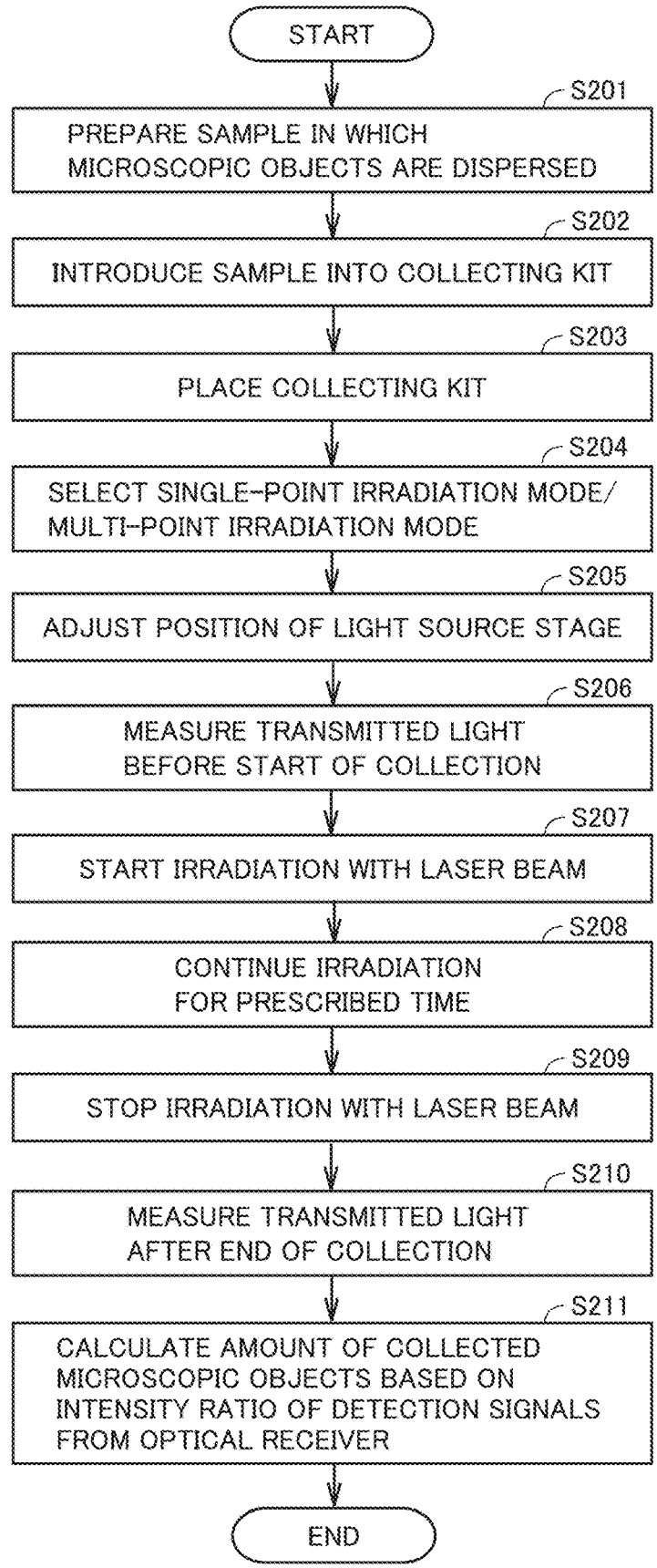
FIG. 17 is a flowchart illustrating a method for collecting microscopic objects in a modification of the first embodiment.

FIG. 17 is a flowchart illustrating a method for collecting microscopic objects in the modification of the first embodiment. The processes in steps S201 to S205 in this flowchart are similar to the corresponding processes (see FIG. 11) in the first embodiment, and thus the description thereof will not be repeated.

Controller 9 controls adjustment mechanism 3 to adjust the position of light source stage 2 according to the control mode selected in S204 (step S205). Then, in S206, controller 9 controls driver 5 so as to irradiate sample SP with weak laser beam L for measuring the intensity of transmitted light before the collection of the microscopic objects. That is, controller 9 acquires intensity RX1 of the detection signal. The laser output at this time can be set to a value, for example, about one or two (or more) orders of magnitude smaller than the laser output for the collection of the microscopic objects. As an example, the laser output for collecting the microscopic objects is 180 mW, whereas the laser output for measuring the intensity of transmitted light can be set to 3 mW.

In subsequent steps S207 to S209, controller 9 controls driver 5 so as to irradiate sample SP with laser beam L for collecting the microscopic objects. These processes are similar to the processes of S106 to S108 in the first embodiment.

In S210, controller 9 controls driver 5 so as to irradiate sample SP with weak laser beam L for measuring the intensity of transmitted light after the collection of the microscopic objects. That is, controller 9 acquires intensity RX2 of the detection signal. The laser output for measuring the intensity of the transmitted light after the collection of the microscopic objects is desirably set to a value equal to the laser output for measuring the intensity of the transmitted light before the collection of the microscopic objects. Thus, a series of processes ends.

This flowchart has described an example in which laser beam L for collecting the microscopic objects and laser beam L for measuring the intensity of transmitted light are different from each other. However, the irradiation with laser beam L for measuring the intensity of transmitted light may be omitted, and the intensity of transmitted light of laser beam L for collecting the microscopic objects may be measured before and after the collection of the microscopic objects.

As described above, in the present modification, the intensity ratio (attenuation ratio) between intensity RX1 before the start of the collection of the microscopic objects and intensity RX2 after the end of the collection is acquired for the detection signal of laser beam L transmitted through sample SP. In the present modification, the correlation between the attenuation ratio of the detection signal of laser beam L (see Expression (1)) and the amount of collected microscopic objects is obtained in advance. Therefore, according to the present modification, an amount of collected microscopic objects can be obtained by calculating the attenuation ratio of the detection signal of laser beam L while using laser beam L to collect the microscopic objects in the liquid.

Note that the acquisition timings of the two detection signals (timings of measuring the intensity of the transmitted light) are not limited to before and after the collection of the microscopic objects, and may be during the collection of the microscopic objects. For example, the first measurement may be performed before the collection of the microscopic objects, and the second measurement may be performed during the collection of the microscopic objects (for example, immediately before the end of the collection). Alternatively, both the first measurement and the second measurement may be performed during the collection of the microscopic objects (for example, immediately after the start and immediately before the end). Alternatively, the first measurement may be performed during the collection of the microscopic objects (for example, immediately after the start), and the second measurement may be performed after the collection of the microscopic objects. In this manner, the intensity ratio of the two detection signals acquired at any timing along with the light irradiation may be calculated.

Second Embodiment

In general, fluorescence imaging is widely used for observing a biological sample such as a microorganism. The second embodiment will describe an example in which the quantitative evaluation method of the amount of collected microscopic objects as described in the first embodiment (or the modification thereof) is combined with fluorescence imaging. In this measurement example, fluorescent beads are used as microscopic objects. The fluorescent beads contain a fluorescent dye of yellow green (YG). The material of the fluorescent beads is polystyrene. The diameter of the fluorescent beads was 1.0 µm. The microscopic objects may be microorganisms (bacteria or the like) stained with a fluorescent dye.

Figure 18:
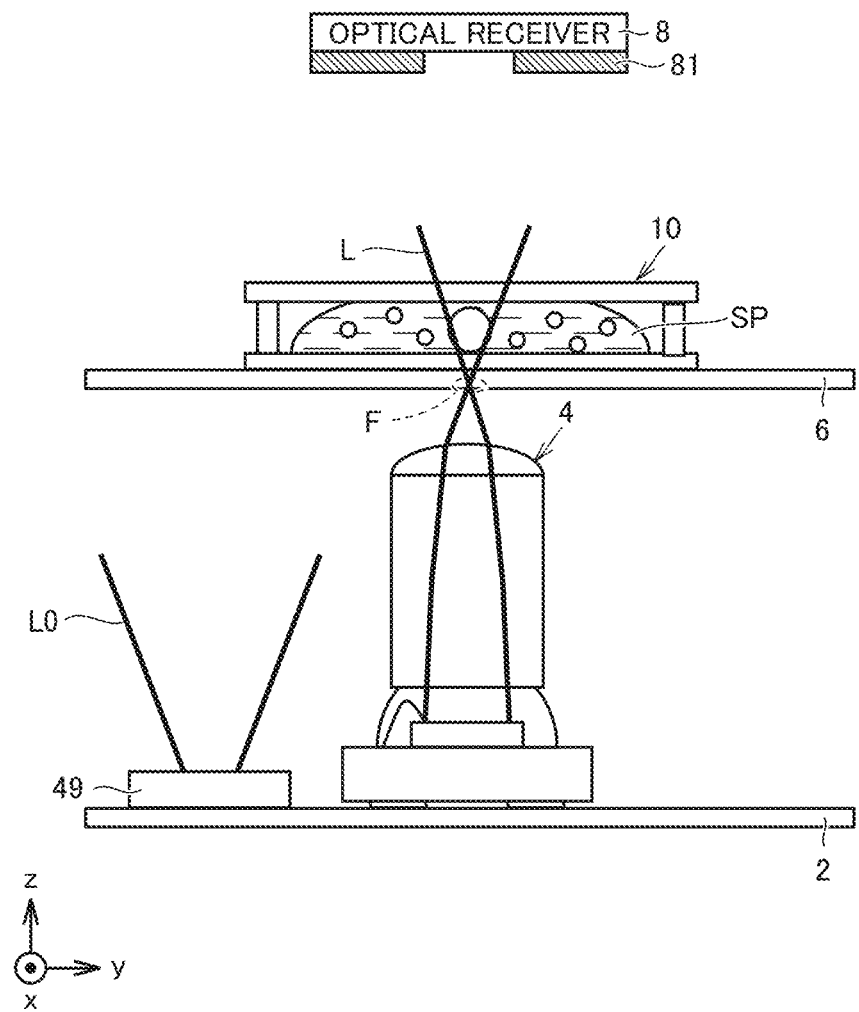
FIG. 18 is a block diagram for describing the feature of a microscopic object detection system according to a second embodiment.

FIG. 18 is a diagram for describing the feature of a microscopic object detection system according to the second embodiment. A detection device for microscopic object according to the second embodiment is different from the configuration of detection device 1 for microscopic object according to the first embodiment (see FIGS. 1 to 4) in further including a fluorescent light source 49 in addition to laser module 4 and further including a mask 81. In this case, laser module 4 and fluorescent light source 49 correspond to a "light source unit" according to the present disclosure. The other configuration of the detection device for microscopic object according to the second embodiment is equal to the corresponding configuration of detection device 1, and thus the description will not be repeated.

Fluorescent light source 49 is mounted on light source stage 2 together with laser module 4. Fluorescent light source 49 emits excitation light L0 (for example, light having a blue wavelength) for exciting the fluorescent dye in the fluorescent beads. Fluorescence (for example, light having a green wavelength) is emitted from the fluorescent beads by irradiation with excitation light L0. Regarding the fluorescent beads used in this measurement, the maximum wavelength of excitation light L0 was 441 nm, and the maximum wavelength of fluorescence was 486 nm. In this example, fluorescent light source 49 is a light emitting diode (LED), but may be another type of light source such as a mercury lamp.

Laser module 4 and fluorescent light source 49 may be integrated. More specifically, laser module 4 may also serve as a light source for collecting the fluorescent beads and a light source for exciting the fluorescent dye. That is, laser module 4 may emit excitation light L0 (for example, blue light instead of near-infrared light) for the fluorescent dye and generate the photothermal effect of thin film 106 by excitation light L0. As a result, the light from laser module 4 can be used in common for collecting the microscopic objects in the liquid, for calculating an amount of collected microscopic objects based on a change over time of the detection signal, and for capturing a fluorescent image.

Mask 81 is provided on the lower surface of optical receiver 8. Mask 81 cuts light (stray light) that does not need to be taken into optical receiver 8 out of fluorescence emitted from the fluorescent beads. As a result, the sensitivity of optical receiver 8 to fluorescence is improved.

Note that, in this example, optical receiver 8 is a multi-pixel type photodetector (CCD, CMOS image sensor, or the like) in order to capture a fluorescent image. However, the fluorescent image is used to confirm the collection state of the fluorescent beads, and is not used to calculate an amount of collected fluorescent beads. Therefore, in the second embodiment, optical receiver 8 of a single pixel type (photodiode or the like) can also be employed.

In this measurement example, three types of samples SP were also prepared. The first sample had $2.02\times10^4$ fluorescent beads. The second sample had $2.02\times10^5$ fluorescent beads. The third sample had $2.02\times10^6$ fluorescent beads. The first to third samples are referred to in order as "reference sample", "tenfold concentration sample" and "hundredfold concentration sample" below. The liquid volume was 20 μL in any sample. The output (laser output) of laser beam L was 180 mW. The irradiation time of laser beam L was set to 180 seconds.

Figure 19:
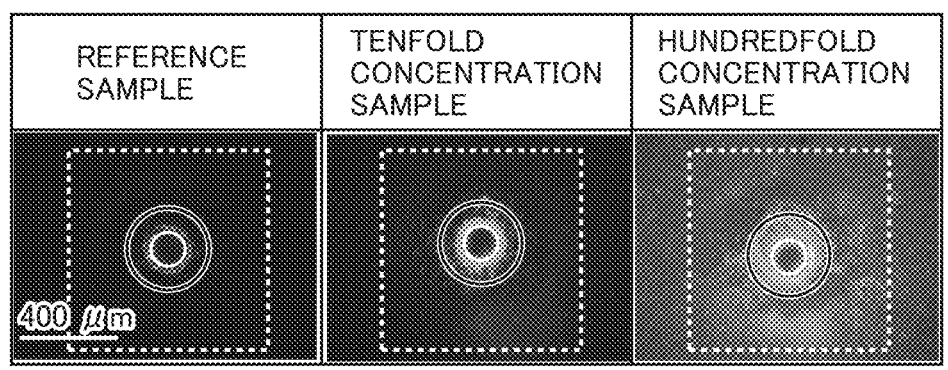
FIG. 19 is a diagram illustrating fluorescent images of samples when irradiation with a laser beam is stopped.

FIG. 19 is a diagram illustrating fluorescent images of samples when irradiation with laser beam L is stopped. A square region indicated by a broken line in the figure is a photometric region (a region where mask 81 is not provided) by optical receiver 8. A circular region indicated by a solid line at the center is an irradiation region (laser spot) irradiated with laser beam L.

As can be seen from FIG. 19, the number of bright spots indicating collection of fluorescent beads (area of collected fluorescent beads) increases as the concentration of fluorescent beads increases. Therefore, the intensity of the detection signal is enhanced as the concentration of the fluorescent beads increases. Accordingly, also in the second embodiment, the slope of the approximate straight line can be calculated from the change in the detection signal (increase rate of the detection signal), and the concentration of the fluorescent beads can be calculated from the slope of the approximate straight line, as in the first embodiment. In addition, as in the modification of the first embodiment, it is also possible to calculate the concentration of the fluorescent beads from the intensity ratio (attenuation ratio or the like) of the detection signals with the change in the detection signal.

It should be understood that the embodiments disclosed herein are illustrative in all respects and not restrictive. The scope of the present disclosure is defined not by the description of the above embodiments but by the claims, and is intended to include meanings equivalent to the claims and all modifications within the scope.

REFERENCE SIGNS LIST

1: detection device, 2: light source stage, 3: adjustment mechanism, 4: laser module, 5: driver, 6: sample holder, 7: filter, 8: optical receiver, 81: mask, 9: controller, 10: collecting kit, 100: detection system, 101: honeycomb substrate, 102: cover substrate, 103: spacer, 104: substrate, 105: honeycomb polymer film, 106: thin film, 107: pore, 108: partition wall, 41: substrate, 411: electrode, 42: surface emitting element, 421: light emitting region, 422: electrode pad, 441: core, 442: cladding, 43: bonding member, 44: optical waveguide, 45: lens, 49: fluorescent light source, X: microscopic object, SP: sample

The invention claimed is:

1. A detection device comprising:
a light source unit that emits light with which a collecting kit is irradiated;
an optical receiver that detects light from a liquid sample held on the collecting kit and outputs a detection signal of the light, the liquid sample including a plurality of microscopic objects; and
a processor that calculates an amount of the plurality of microscopic objects collected in the liquid sample based on a change of the detection signal over time, the change including (i) a slope of an approximate straight line obtained by regression in a time domain of the detection signal of a predetermined period after start of light irradiation of a photothermal conversion region, or (ii) an intensity ratio of two detection signals acquired along with light irradiation of the photothermal conversion region; wherein
the detection device detects the plurality of microscopic objects in the liquid sample by collecting the plurality of microscopic objects dispersed in the liquid sample with the collecting kit, the collecting kit having the photothermal conversion region that converts light into heat and being configured to hold the liquid sample on the photothermal conversion region.

2. The detection device according to claim 1, wherein the light source heats the liquid sample by light irradiation of the photothermal conversion region to generate a bubble at a light irradiation position and generate convection in the liquid sample, and thereby collects the plurality of microscopic objects around the bubble.

3. The detection device according to claim 1, wherein the optical receiver is a single-pixel type photodetector.

4. The detection device according to claim 1, wherein
the plurality of microscopic objects emits fluorescence when excited; and
the light source unit includes:
a laser light source that emits a laser beam with which the collecting kit is irradiated, and
a fluorescent light source that emits light for exciting the plurality of microscopic objects.

5. The detection device according to claim 4, wherein the laser light source and the fluorescent light source are integrated.

6. The detection device according to claim 4, wherein the optical receiver includes a mask that cuts light that does not need to be taken into the optical receiver in fluorescence emitted from the plurality of microscopic objects.

7. The detection device according to claim 1, wherein
the light source unit includes a plurality of light emitting regions and emits a plurality of laser beams from the plurality of light emitting regions,
the detection device further includes:
a holder that holds the collecting kit;
a condenser lens that collects the plurality of laser beams at a same focal point;
an adjustment mechanism that adjusts a relative positional relationship between the holder and the condenser lens; and
a controller that controls the adjustment mechanism,
the controller is configured to switch between a single-point irradiation mode and a multi-point irradiation mode, each of which is a mode for irradiating the photothermal conversion region with at least a part of the plurality of laser beams,
the single-point irradiation mode is a mode for controlling the adjustment mechanism so that the focal point coincides with the photothermal conversion region, and
the multi-point irradiation mode is a mode for controlling the adjustment mechanism so that the focal point is outside the photothermal conversion region.

8. The detection device according to claim 7, wherein the light source unit includes a vertical cavity surface emitting laser.

9. The detection device according to claim 7, wherein
the condenser lens includes a graded-index optical fiber and a plano-convex lens; and
the optical fiber has a first end covering the plurality of light emitting regions and a second end bonded to a flat surface side of the plano-convex lens.

10. A microscopic object detection system comprising:
a collecting kit that has a photothermal conversion region that converts light into heat, the collecting kit being configured to hold a liquid sample on the photothermal conversion region; and a detection device that detects a plurality of microscopic objects in the liquid sample by collecting the plurality of microscopic objects dispersed in the liquid sample using the collecting kit, the detection device including:
- a light source unit that emits light with which the collecting kit is irradiated;
- an optical receiver that detects light from the liquid sample held on the collecting kit and outputs a detection signal of the light; and
- a processor that calculates an amount of the plurality of microscopic objects collected in the liquid sample based on a change of the detection signal over time, the change including (i) a slope of an approximate straight line obtained by regression in a time domain of the detection signal of a predetermined period after start of light irradiation of the photothermal conversion region, or (ii) an intensity ratio of two detection signals acquired along with light irradiation of the photothermal conversion region.

11. The microscopic object detection system according to claim 10, wherein the collecting kit further includes:
- a first surface on which the photothermal conversion region is disposed,
- a second surface that holds the liquid sample between the first surface and the second surface, and
- a spacer for fixing a distance between the first surface and the second surface.

12. A detection method for detecting a plurality of microscopic objects in a liquid sample by collecting the plurality of microscopic objects dispersed in the liquid sample using a collecting kit, the collecting kit having a photothermal conversion region that converts light into heat and being configured to hold the liquid sample on the photothermal conversion region, the detection method comprising:
- irradiating the collecting kit with light;
- detecting light from the liquid sample held on the collecting kit with an optical receiver; and
- calculating an amount of the plurality of microscopic objects collected in the liquid sample based on a change over time of a detection signal from the optical receiver, the change including (i) a slope of an approximate straight line obtained by regression in a time domain of the detection signal of a predetermined period after start of light irradiation of the photothermal conversion region, or (ii) an intensity ratio of two detection signals acquired along with light irradiation of the photothermal conversion region.

* * * * *